US012637725B2

(12) United States Patent
Chan et al.

(10) Patent No.: US 12,637,725 B2
(45) Date of Patent: May 26, 2026

(54) METHODS, OLIGONUCLEOTIDES, AND KITS FOR DETECTION AND TREATMENT OF CORONAVIRUS

(71) Applicant: THE TRANSLATIONAL GENOMICS RESEARCH INSTITUTE, Phoenix, AZ (US)

(72) Inventors: Puiyee Agnes Chan, Phoenix, AZ (US); Nicholas J. Schork, Phoenix, AZ (US); Yongwook Choi, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 349 days.

(21) Appl. No.: 17/914,319

(22) PCT Filed: Mar. 26, 2021

(86) PCT No.: PCT/US2021/010015
§ 371 (c)(1),
(2) Date: Sep. 23, 2022

(87) PCT Pub. No.: WO2021/194603
PCT Pub. Date: Sep. 30, 2021

(65) Prior Publication Data
US 2025/0019778 A1 Jan. 16, 2025

Related U.S. Application Data

(60) Provisional application No. 63/004,838, filed on Apr. 3, 2020, provisional application No. 63/000,476, filed on Mar. 26, 2020.

(51) Int. Cl.
*C12Q 1/70* (2006.01)
*C12Q 1/6851* (2018.01)

(52) U.S. Cl.
CPC ........... *C12Q 1/701* (2013.01); *C12Q 1/6851* (2013.01)

(58) Field of Classification Search
None
See application file for complete search history.

(56) References Cited

U.S. PATENT DOCUMENTS

2005/0095582 A1 5/2005 Gillim-Ross et al.

FOREIGN PATENT DOCUMENTS

WO 2005/017133 A1 2/2005
WO 2006/136448 A2 12/2006

OTHER PUBLICATIONS

Baranov,. Pavel V; et al; "Programmed ribosomal frameshifting in decoding the SARS-CoV genome" Virology, 332, 498-510, 2005 (Year: 2005).*

(Continued)

*Primary Examiner* — David W Berke-Schlessel
(74) *Attorney, Agent, or Firm* — FULLER IP LAW LLC; Rodney J. Fuller

(57) ABSTRACT

Methods, kits, and oligonucleotides used in the detection of coronavirus, including severe acute respiratory syndrome coronavirus 2 (SARS-CoV-2), are disclosed. In some aspects, the oligonucleotides are primers or probes used in the described methods or kits. The nucleotide sequence of the oligonucleotide consists of 300 or less, 150 or less, or 40 or less continuous nucleotides from a nucleotide sequence selected from the group consisting of: SEQ ID NO:1, SEQ ID NO:2, SEQ ID NO:3, SEQ ID NO:4, and SEQ ID NO: 5, or is a variant thereof. In some embodiments, the oligonucleotide is modified with an internal spacer or a detectable label. For example, the 5' terminus is labeled with a fluorophore and the 3' terminus is complexed to a quencher of fluorescence of said fluorophore. In some embodiments, the (Continued)

nucleotide sequence of the oligonucleotide further comprises a universal tail sequence.

8 Claims, 22 Drawing Sheets

Specification includes a Sequence Listing.

(56) References Cited

OTHER PUBLICATIONS

Abolnik, Celia; "Genomic and single nucleotide polymorphism analysis of infectious bronchitis coronavirus" Infection, Genetics and Evolution, 32, 416-424, 2015 (Year: 2015).*

Guo, Xi; et al; "Development of a Single Nucleotide Polymorphism DNA Microarray for the Detection and Genotyping of the SARS Coronavirus" Journal of Microbiology and Biotechnology, 24, 1445-1454, 2014 (Year: 2014).*

Chu et al,, "Molecular Diagnosis of a Novel Coronavirus (2019-nCoV) Causing an Outbreak of Pneumonia", Clinical Chemistry, 66(4):549-555 (Jan. 31, 2020).

Mukherjee et al., "Global cataloguing of variations in untranslated regions of viral genome and prediction of key host RNA binding protein-microRNA interactions modulating genome stability in SARS-CoV-2", PLoS One, 15(8):e0237559 pp. 1-20 (Aug. 11, 2020).

* cited by examiner

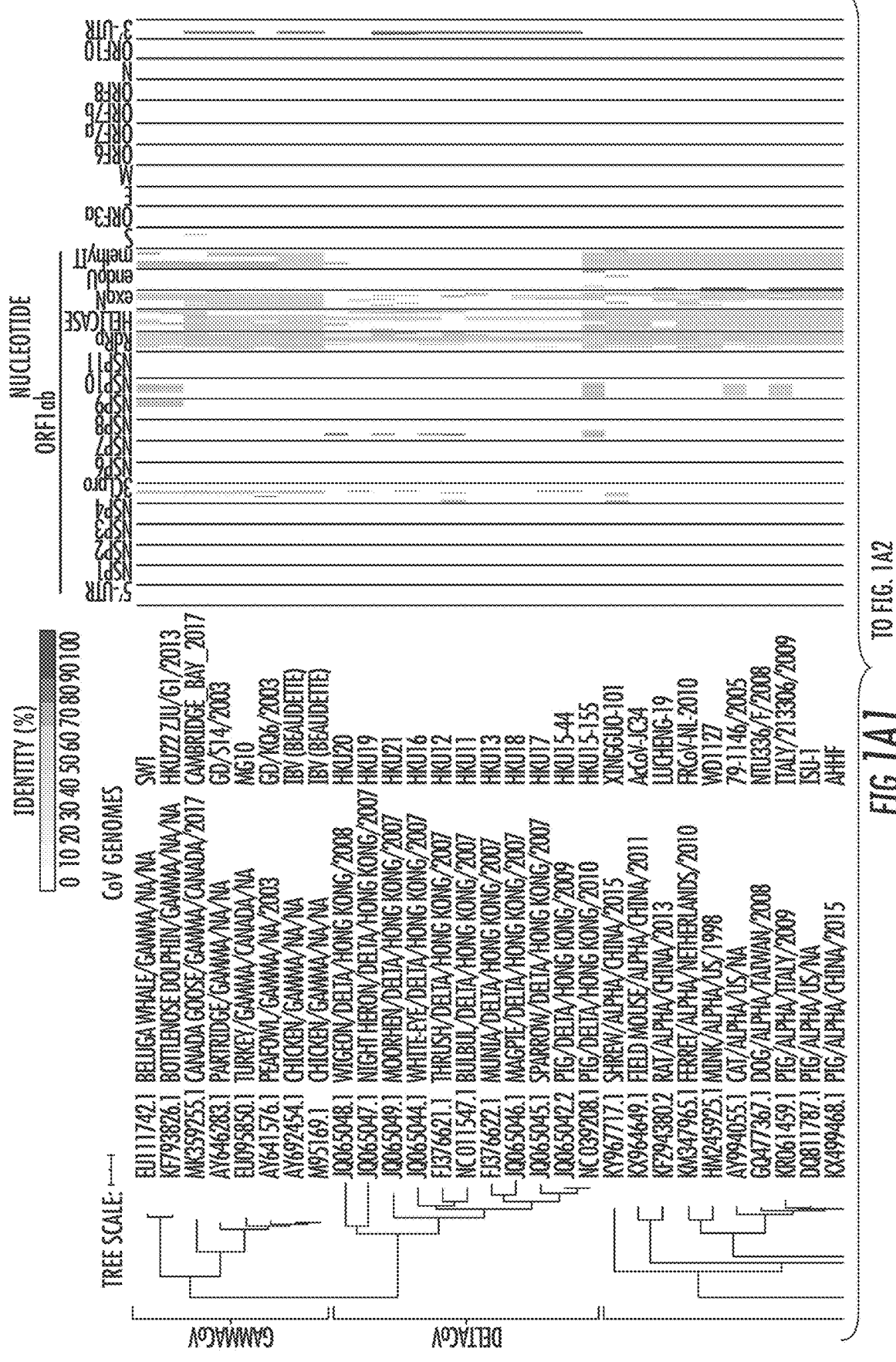
FIG. 1A1
TO FIG. 1A2

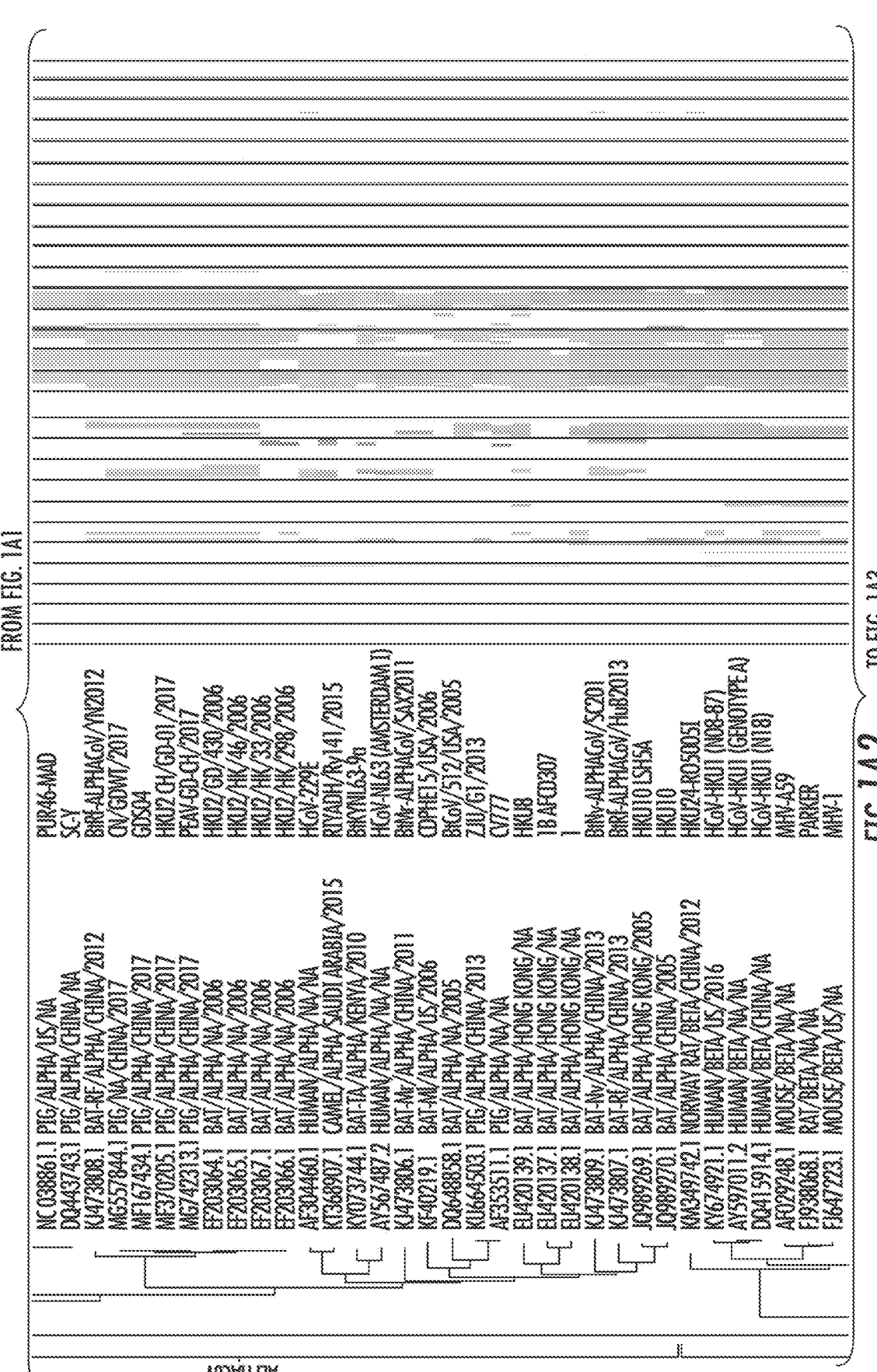
FIG. 1A2

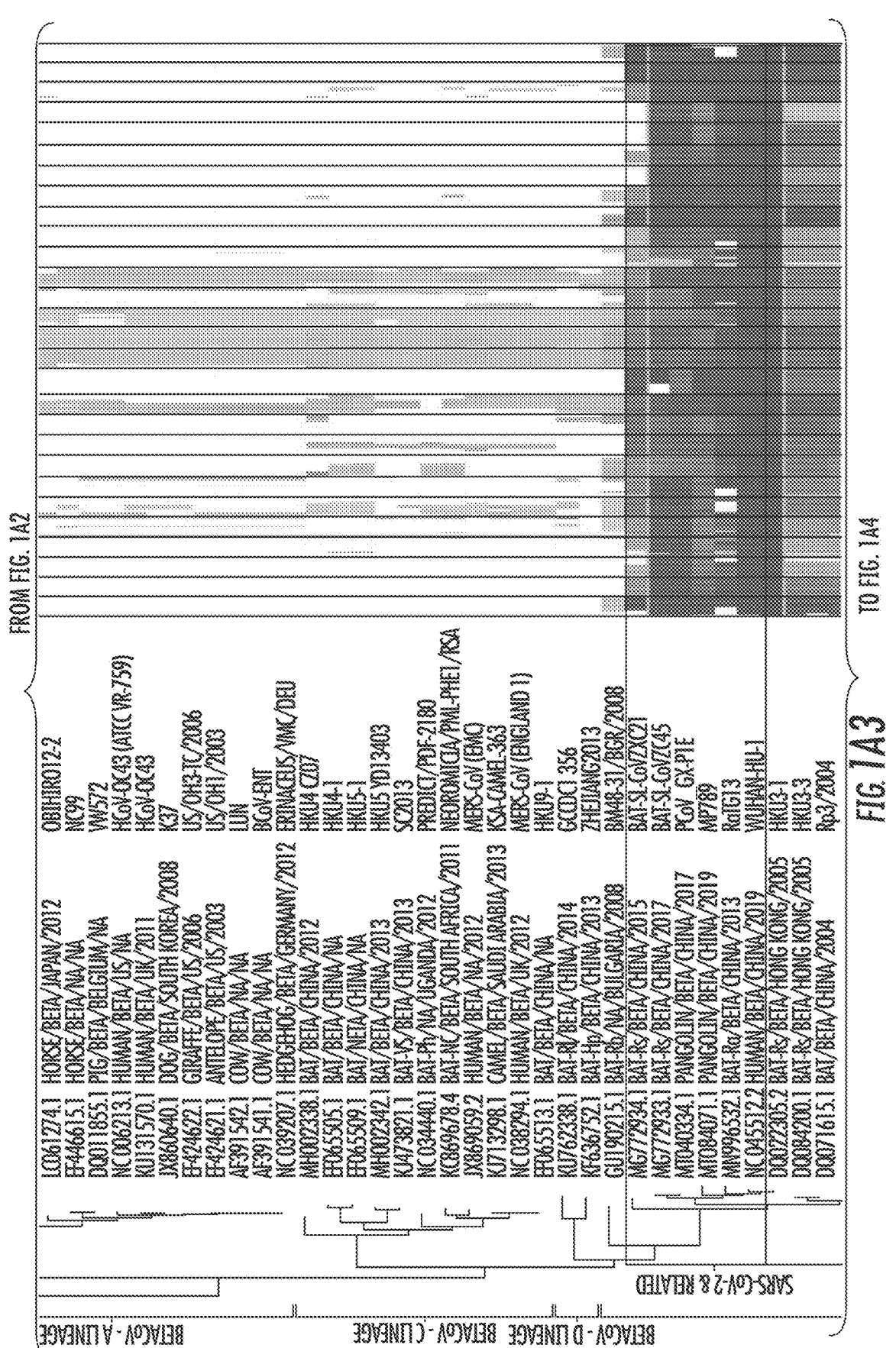
FIG. 1A3

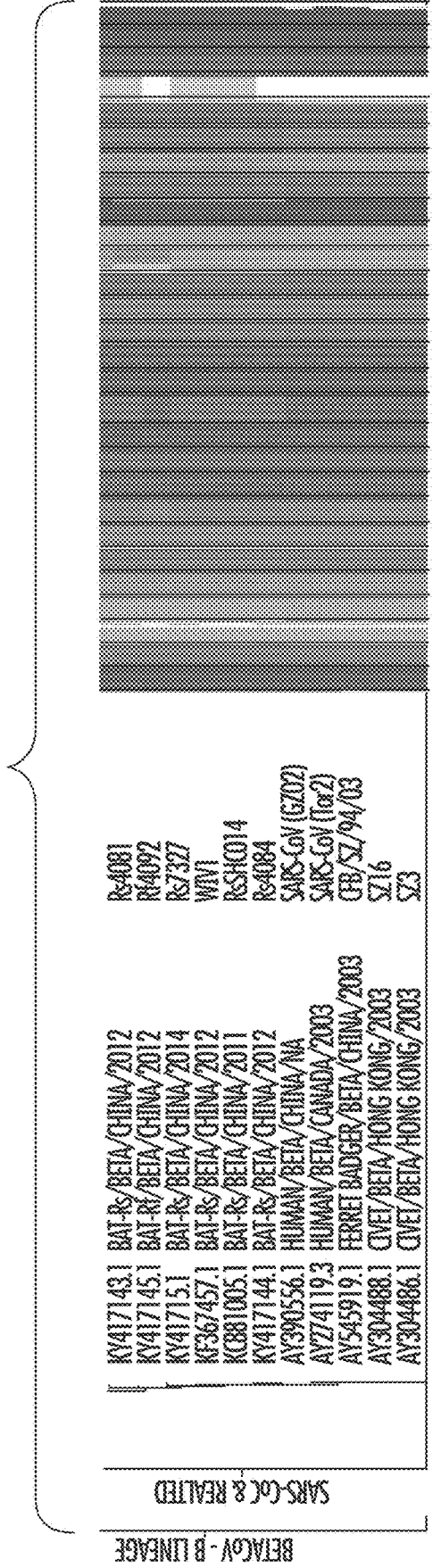
FIG. 1A4

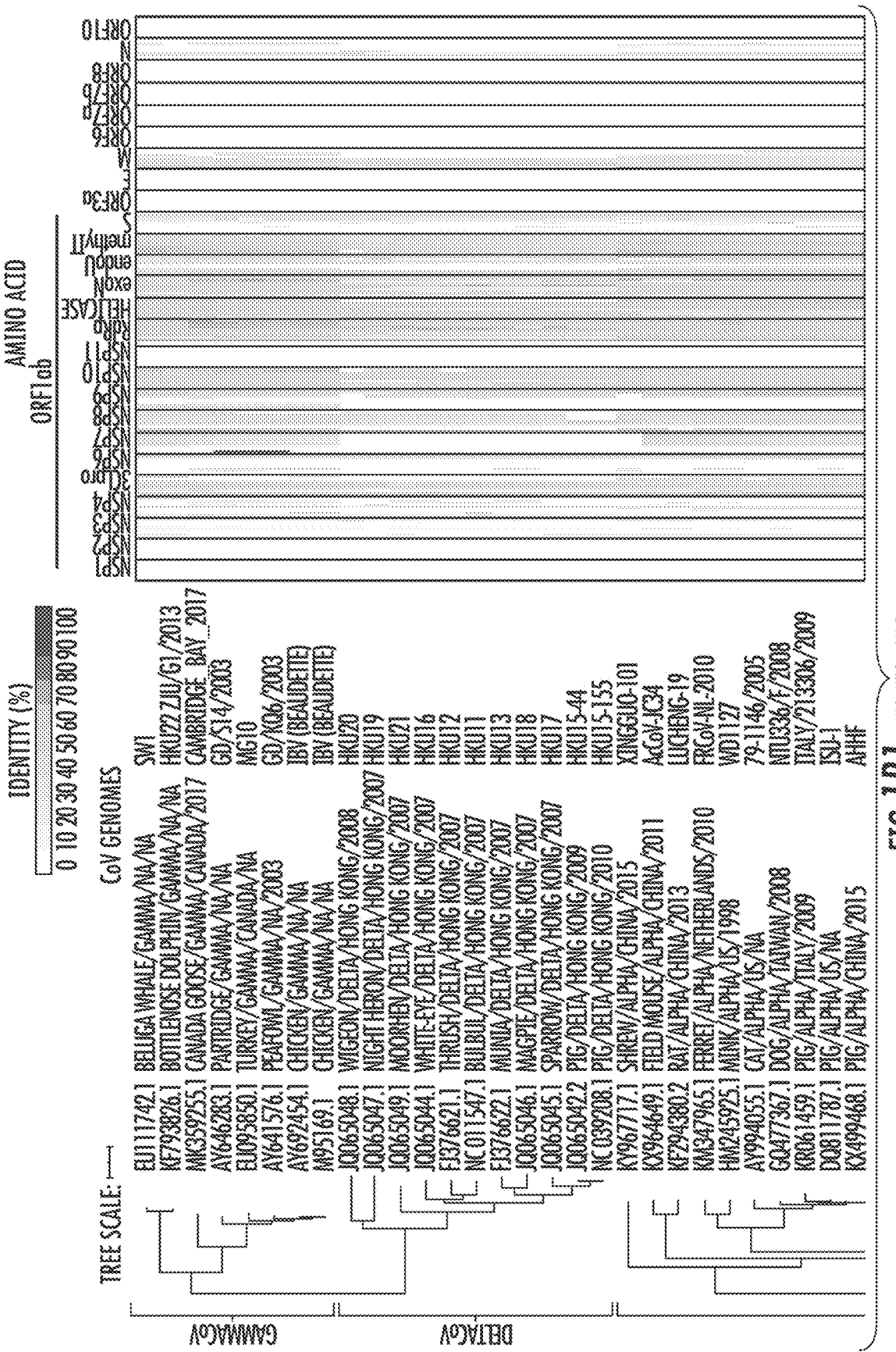
FIG. 1B1    TO FIG. 1B2

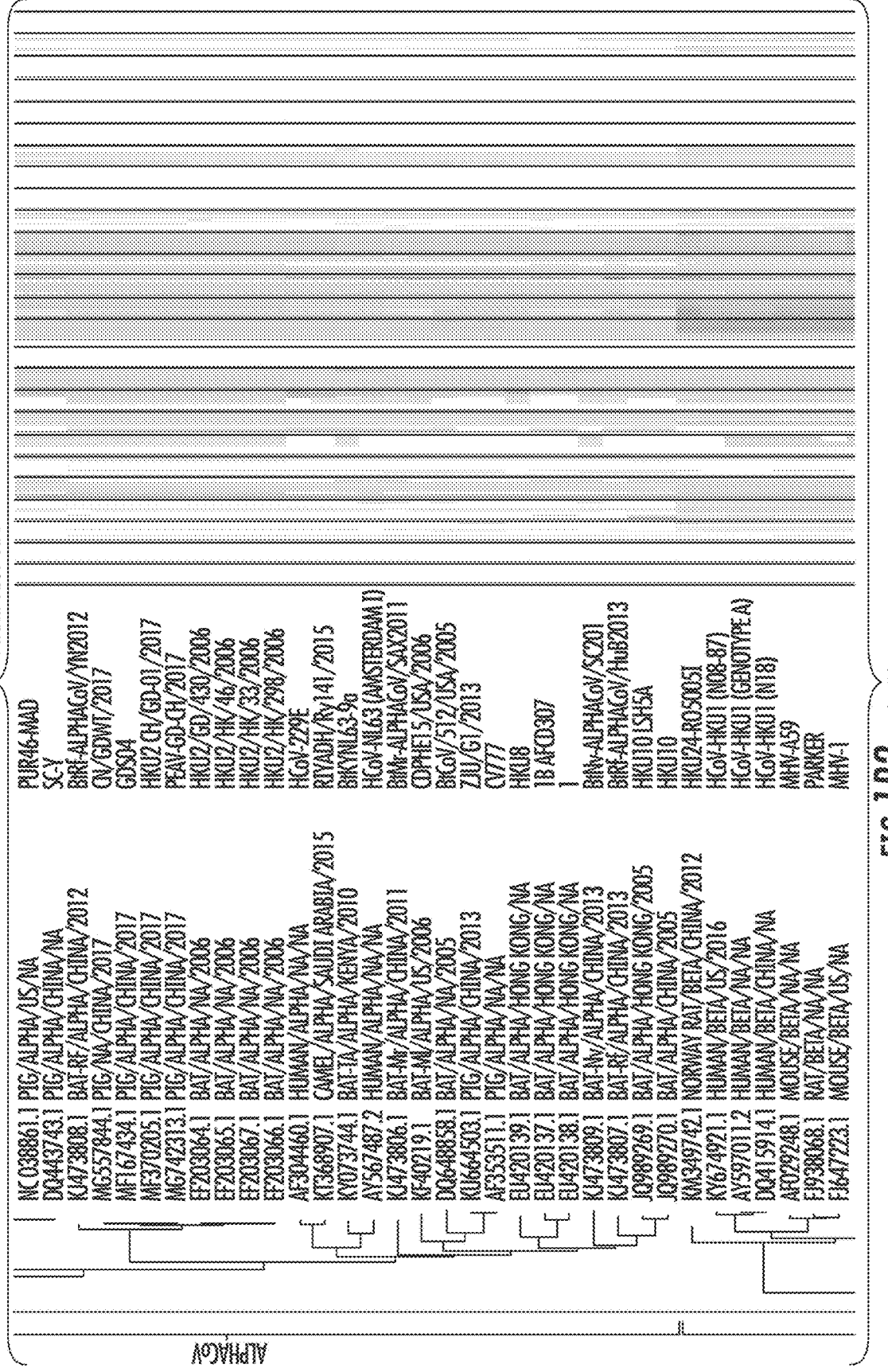
FIG. 1B2

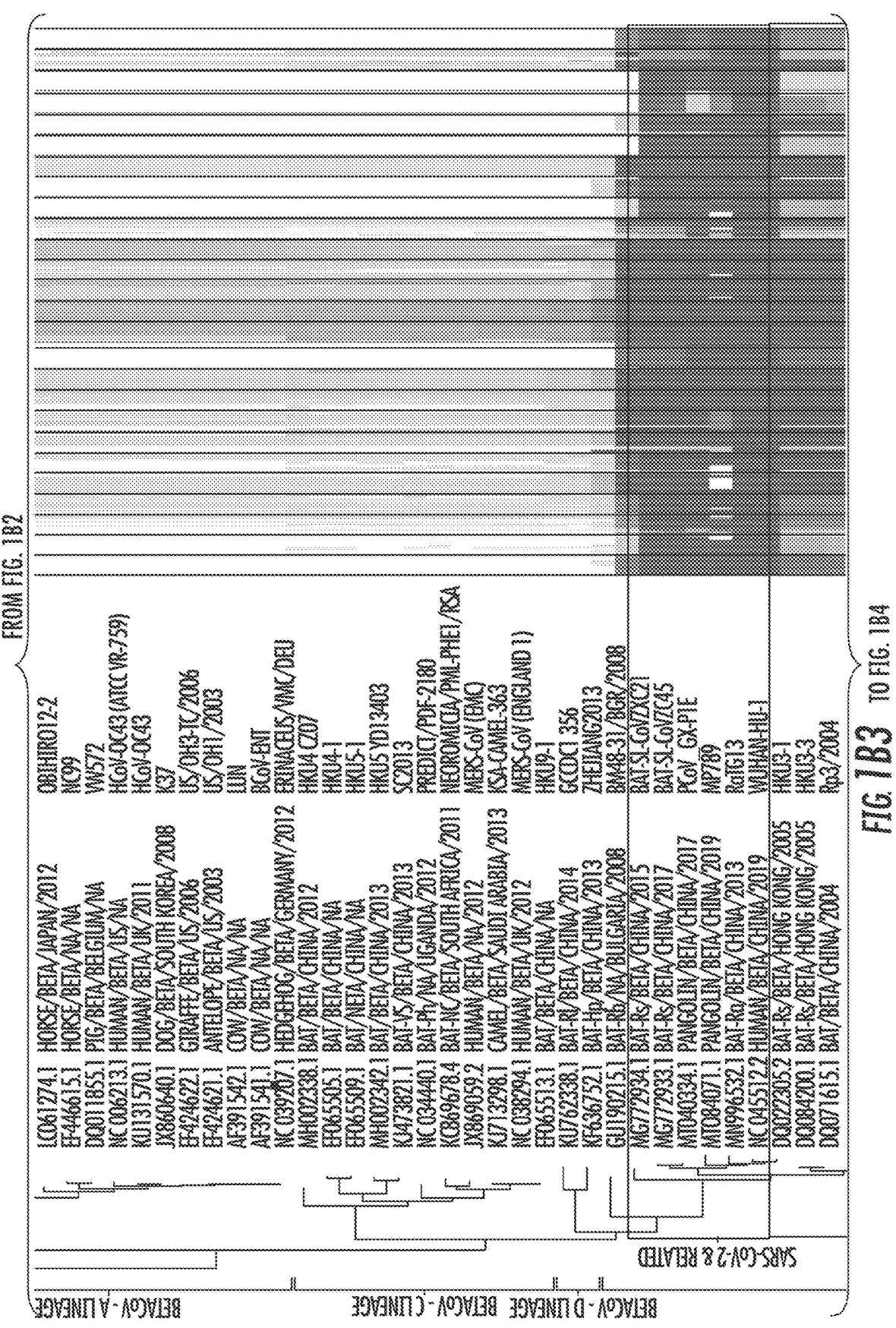
*FIG. 1B3*

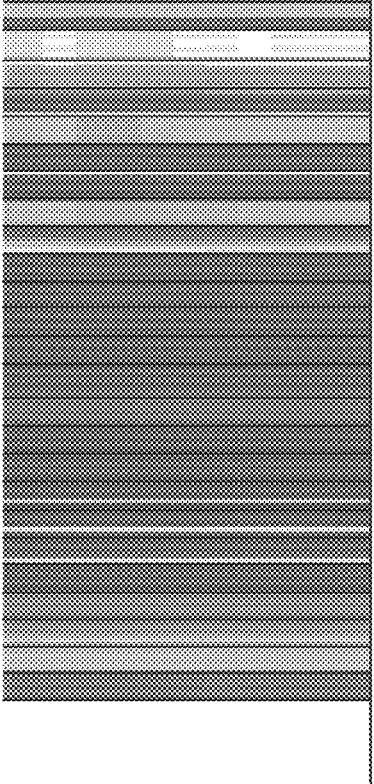

FROM FIG. 1B3

FIG. 1B4

KY417143.1 BAT-Rs/BETA/CHINA/2012 Rs4081
KY417145.1 BAT-Rs/BETA/CHINA/2012 Rs4092
KY4715.1 BAT-Rs/BETA/CHINA/2014 Rs7327
KF367457.1 BAT-Rs/BETA/CHINA/2012 WIV1
KC881005.1 BAT-Rs/BETA/CHINA/2011 RsSHC014
KY417144.1 BAT-Rs/BETA/CHINA/2012 Rs4084
AY390556.1 HUMAN/BETA/CHINA/NA SARS-CoV (GZ02)
AY274119.3 HUMAN/BETA/CANADA/2003 SARS-CoV (Tor2)
AY545919.1 FERRET BADGER/BETA/CHINA/2003 CFB/SZ/94/03
AY304488.1 CIVET/BETA/HONG KONG/2003 SZ16
AY304486.1 CIVET/BETA/HONG KONG/2003 SZ3

SARS-CoV & RELATED

BETACoV - B LINEAGE

FIG. 2C

FROM FIG. 2F

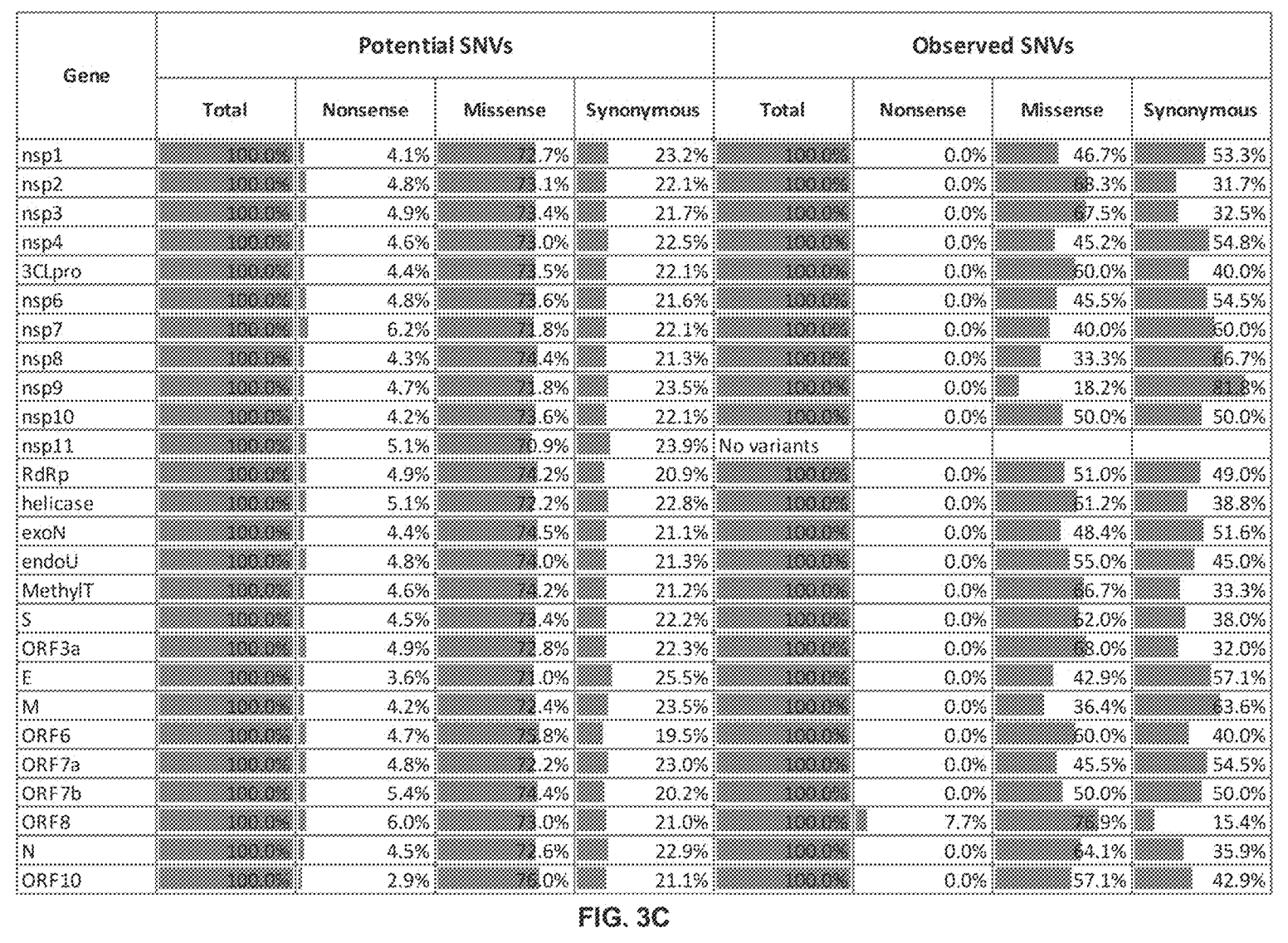

| Gene | Potential SNVs | | | | Observed SNVs | | | |
|---|---|---|---|---|---|---|---|---|
| | Total | Nonsense | Missense | Synonymous | Total | Nonsense | Missense | Synonymous |
| nsp1 | | 4.1% | 72.7% | 23.2% | | 0.0% | 46.7% | 53.3% |
| nsp2 | | 4.8% | 73.1% | 22.1% | | 0.0% | 68.3% | 31.7% |
| nsp3 | | 4.9% | 73.4% | 21.7% | | 0.0% | 67.5% | 32.5% |
| nsp4 | | 4.6% | 72.9% | 22.5% | | 0.0% | 45.2% | 54.8% |
| 3CLpro | | 4.4% | 73.5% | 22.1% | | 0.0% | 60.0% | 40.0% |
| nsp6 | | 4.8% | 73.6% | 21.6% | | 0.0% | 45.5% | 54.5% |
| nsp7 | | 6.2% | 71.8% | 22.1% | | 0.0% | 40.0% | 60.0% |
| nsp8 | | 4.3% | 74.4% | 21.3% | | 0.0% | 33.3% | 66.7% |
| nsp9 | | 4.7% | 71.8% | 23.5% | | 0.0% | 18.2% | 81.8% |
| nsp10 | | 4.2% | 73.6% | 22.1% | | 0.0% | 50.0% | 50.0% |
| nsp11 | | 5.1% | 70.9% | 23.9% | No variants | | | |
| RdRp | | 4.9% | 74.2% | 20.9% | | 0.0% | 51.0% | 49.0% |
| helicase | | 5.1% | 72.1% | 22.8% | | 0.0% | 61.2% | 38.8% |
| exoN | | 4.4% | 74.5% | 21.1% | | 0.0% | 48.4% | 51.6% |
| endoU | | 4.8% | 73.9% | 21.3% | | 0.0% | 55.0% | 45.0% |
| MethylT | | 4.6% | 74.2% | 21.2% | | 0.0% | 46.7% | 33.3% |
| S | | 4.5% | 73.4% | 22.2% | | 0.0% | 62.0% | 38.0% |
| ORF3a | | 4.9% | 72.8% | 22.3% | | 0.0% | 68.0% | 32.0% |
| E | | 3.6% | 71.0% | 25.5% | | 0.0% | 42.9% | 57.1% |
| M | | 4.2% | 72.4% | 23.5% | | 0.0% | 36.4% | 63.6% |
| ORF6 | | 4.7% | 75.8% | 19.5% | | 0.0% | 60.0% | 40.0% |
| ORF7a | | 4.8% | 72.2% | 23.0% | | 0.0% | 45.5% | 54.5% |
| ORF7b | | 5.4% | 74.4% | 20.2% | | 0.0% | 50.0% | 50.0% |
| ORF8 | | 6.0% | 73.0% | 21.0% | | 7.7% | 76.9% | 15.4% |
| N | | 4.5% | 72.6% | 22.9% | | 0.0% | 64.1% | 35.9% |
| ORF10 | | 2.9% | 76.0% | 21.1% | | 0.0% | 57.1% | 42.9% |

FIG. 3C

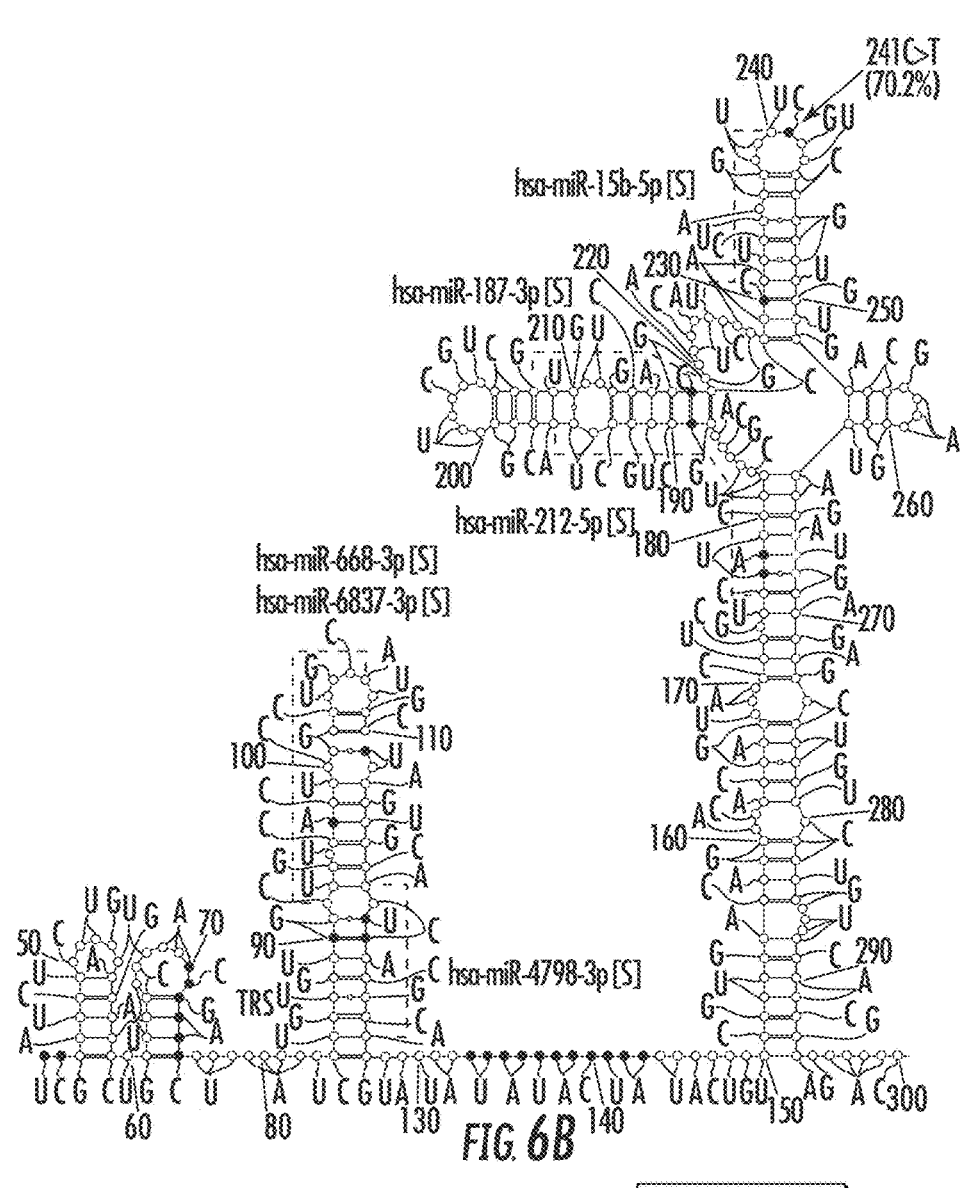

FIG. 6B

MUTATION ESCAPE

| H1N1 NS1 C112A MUTANT | 84 - 5′ | GATGCCCCATTCCTTGATCGGCTCCGCAGAGA 3′ - 116 |
| H1N1 NS1 WILD TYPE | 84 - 5′ | GATGCCCCATTCCTTGATCGGCTCCGCCGAGA 3′ - 116 |
| hsa-miR-1307-3p | | 22 - 3′  gugcuggcugcggugcggcuca 5′ - 1 |
| SARS-CoV-2 3′-UTR | 29731 - 5′ | ACCGAGGCCACGCGGAGT 3′ - 29748 |

| POSITION (nt) | 29734 | 29742 | 29744 |
|---|---|---|---|
| SARS-CoV-2 | BIALLELIC VARIANT<br>REF: G<br>Var1: G>C 0.90% | TRIALLELIC VARIANT<br>REF: G<br>Var1: G>A 0.76%<br>Var2: G>T 1.27% | INTERRUPTION OF PREDICTED miR-1307-3p 5′-END BASE-PAIRING |
| INFLUENZA H1N1 | N.A. | N.A. | MUTATION ESCAPE |

FIG. 6C

SEQUENCE LISTING

<160> NUMBER OF SEQ ID NOS: 20

<210> SEQ ID NO 1
<211> LENGTH: 346
<212> TYPE: DNA
<213> ORGANISM: Severe Acute Respiratory Syndrome Coronavirus 2

<400> SEQUENCE: 1
atgggctata taaacgtttt cgcttttccg tttacgatat atagtctact cttgtgcaga       60
atgaattctc gtaactacat agcacaagta gatgtagtta actttaatct cacatagcaa      120

-continued

```
tctttaatca gtgtgtaaca ttagggagga cttgaaagag ccaccacatt ttcaccgagg      180
ccacgcggag tacgatcgag tgtacagtga acaatgctag ggagagctgc ctatatggaa      240
gagccctaat gtgtaaaatt aattttagta gtgctatccc catgtgattt taatagcttc      300
ttaggagaat gacaaaaaaa aaaaaaaaaa aaaaaaaaaa aaaaaa                      346

<210> SEQ ID NO 2
<211> LENGTH: 332
<212> TYPE: DNA
<213> ORGANISM: Bat Coronavirus

<400> SEQUENCE: 2
atgggctata taaacgtttt cgcttttccg tttacgatat atagtctact cttgtgcaga       60
atgaattctc gtaactacat agcacaagta gatgtagtta accttaatct cacatagcaa      120
tctttaatca gtgtgtaaca ttagggagga cttgaaagag ccaccacatt ttcaccgagg      180
ccacgcggag tacgatcgag ggtacagtga ataatgctag ggagagctgc ctatatggaa      240
gagccctaat gtgtaaaatt aattttagta gtgctatccc atgtgatttt aatagcttct      300
taggagaatg acaaaaaaaa aaaaaaaaaa aa                                     332

<210> SEQ ID NO 3
<211> LENGTH: 178
<212> TYPE: DNA
<213> ORGANISM: Pangolin Coronavirus

<400> SEQUENCE: 3
atgggctata taaacgtttt cgcttttccg tttacgatat atagtctact cttgtgcaga       60
atgaattctc gtagctacat agcacaagta gatgtagtta actttaatct cacatagcaa      120
tctttaatca gtgtgtaaca ttagggagga cttgaaagag ccaccacatt ttcaccga       178

<210> SEQ ID NO 4
<211> LENGTH: 339
<212> TYPE: DNA
<213> ORGANISM: Bat Coronavirus

<400> SEQUENCE: 4
atgggctata taaacgtttt cgctttccgt ttacgatata tagtctactc ttgtgcagaa       60
tgaattctcg taactacata gcacaagtag atgtagttaa ctttaatctc acatagcaat      120
ctttaatcaa tgtgtaacat tagggaggat ttgaaagagc caccacgttc tcaccgaggc      180
cacgcggagt acgatcgagg gtacagtgaa taatgttagg gagagcagcc tatatggaag      240
agccctaatg tgtaaaatta attttagtag tgctatcccc atgtgatttt aatagcttca      300
accactcgac aagaaaaaaa aaaaaaaaaa aaaaaaaaa                              339

<210> SEQ ID NO 5
<211> LENGTH: 340
<212> TYPE: DNA
<213> ORGANISM: Bat Coronavirus

<400> SEQUENCE: 5
atgggctata taaacgtttt cgcttttccg tttacgatat atagtctact cttgtgcaga       60
atgaattctc gtaactacat agcacaagta gatgtagtta actttaattt cacatagcaa      120
tctttaatca atgtgtaaca ttggggagga cttgaaagag ccaccacgtt ttcaccgagg      180
ccacgcggag tacgatcgag ggtacagcca ataatgttag ggagagcagc ctatatggaa      240
```
gagccctaat gtgtaaaatt aattttagta gtgctatccc catgtgattt taatagcttc        300
aaccactcga caagaaaaaa aaaaaaaaa aaaaaaaaa                                  340

<210> SEQ ID NO 6
<211> LENGTH: 337
<212> TYPE: DNA
<213> ORGANISM: Human Severe Acute Respiratory Syndrome Coronavirus Tor2

<400> SEQUENCE: 6
atgggctatg taaacgtttt cgcaattccg tttacgatac atagtctact cttgtgcaga        60
atgaattctc gtaactaaac agcacaagta ggtttagtta actttaatct cacatagcaa        120
tctttaatca atgtgtaaca ttagggagga cttgaaagag ccaccacatt ttcatcgagg        180
ccacgcggag tacgatcgag ggtacagtga ataatgctag ggagagctgc ctatatggaa        240
gagccctaat gtgtaaaatt aattttagta gtgctatccc catgtgattt taatagcttc        300
ttaggagaat gacaaaaaaa aaaaaaaaa aaaaaaa                                   337

<210> SEQ ID NO 7
<211> LENGTH: 293
<212> TYPE: DNA
<213> ORGANISM: Artificial Sequence
<220> FEATURE:
<223> OTHER INFORMATION: Recombinant ExoN1

<400> SEQUENCE: 7
atgggctatg taaacgtttt cgcaattccg tttacgatat atagtctact cttgtgcaga        60
atgaattctc gtaactaaac agcacaagta ggtttagtta actttaatct cacatagcaa        120
tctttaatca atgtgtaaca ttagggagga cttgaaagag ccaccacatt ttcatcgagg        180
ccacgcggag tacgatcgag ggtacagtga ataatgctag ggagagctgc ctatatggaa        240
gagccctaat gtgtaaaatt aattttagta gtgctatccc catgtgattt taa               293

<210> SEQ ID NO 8
<211> LENGTH: 337
<212> TYPE: DNA
<213> ORGANISM: Bat Coronavirus

<400> SEQUENCE: 8
atgggctatg taaacgtttt cgcaattccg tttacgatac atagtctact cttgtgcaga        60
atgaattctc gtagctaaac agcacaagta ggtttagtta actttaatct cacatagcaa        120
tctttaatca atgtgtaaca ttagggagga cttgaaagag ccaccacatt ttcaccgagg        180
ccacgcggag tacgatcgag ggtacagtga ataatgctag ggagagctgc ctatatggaa        240
gagccctaat gtgtaaaatt aattttagta gtgctatccc catgtgattt taatagcttc        300
ttaggagaat gacaaaaaaa aaaaaaaaa aaaaaaa                                   337

<210> SEQ ID NO 9
<211> LENGTH: 33
<212> TYPE: DNA
<213> ORGANISM: Chicken Infectious Bronchitis Virus

<400> SEQUENCE: 9
ccggggccac gcggagtacg atcgagggta cag                                      33

<210> SEQ ID NO 10
<211> LENGTH: 33
<212> TYPE: DNA
<213> ORGANISM: Chicken Infectious Bronchitis Virus -continued

<400> SEQUENCE: 10
ccgaggccac gcggagtacg atcgagggta cag                                    33

<210> SEQ ID NO 11
<211> LENGTH: 149
<212> TYPE: RNA
<213> ORGANISM: Homo sapiens

<400> SEQUENCE: 11
caucaagacc cagcugaguc acugucacug ccuaccaauc ucgaccggac cucgaccggc       60
ucgucugugu ugccaaucga cucggcgugg cgucggucgu gguagauagg cggucaugca      120
uacgaauuuu cagcucuugu ucuggugac                                       149

<210> SEQ ID NO 12
<211> LENGTH: 22
<212> TYPE: RNA
<213> ORGANISM: Homo sapiens

<400> SEQUENCE: 12
acucggcgug gcgucggucg ug                                               22

<210> SEQ ID NO 13
<211> LENGTH: 91
<212> TYPE: RNA
<213> ORGANISM: Homo sapiens

<400> SEQUENCE: 13
aaacacuuga gcccagcggu uugaggcuac agugagaugu gauccugcca caucucacug       60
uagccucgaa ccccugggcu caagugauuc a                                     91

<210> SEQ ID NO 14
<211> LENGTH: 22
<212> TYPE: RNA
<213> ORGANISM: Homo sapiens

<400> SEQUENCE: 14
ucucacugua gccucgaacc cc                                               22

<210> SEQ ID NO 15
<211> LENGTH: 10
<212> TYPE: DNA
<213> ORGANISM: Severe Acute Respiratory Syndrome Coronavirus 2
<220> FEATURE:
<221> NAME/KEY: misc_feature
<222> LOCATION: (1)..(1)
<223> OTHER INFORMATION: n is A, C, or absent
<220> FEATURE:
<221> NAME/KEY: misc_feature
<222> LOCATION: (6)..(6)
<223> OTHER INFORMATION: n is C or T
<220> FEATURE:
<221> NAME/KEY: misc_feature
<222> LOCATION: (10)..(10)
<223> OTHER INFORMATION: n is G or T

<400> SEQUENCE: 15 ntttantagn                                                             10

<210> SEQ ID NO 16
<211> LENGTH: 10
<212> TYPE: DNA

-continued

```
<213> ORGANISM: Bat Coronavirus
<220> FEATURE:
<221> NAME/KEY: misc_feature
<222> LOCATION: (2)..(2)
<223> OTHER INFORMATION: n is absent

<400> SEQUENCE: 16 anttactaga                                                              10

<210> SEQ ID NO 17
<211> LENGTH: 10
<212> TYPE: DNA
<213> ORGANISM: Bat Coronavirus

<400> SEQUENCE: 17
atttactaga                                                             10

<210> SEQ ID NO 18
<211> LENGTH: 10
<212> TYPE: DNA
<213> ORGANISM: Human Severe Acute Respiratory Syndrome Coronavirus Tor2

<400> SEQUENCE: 18
gaacaacgta                                                             10

<210> SEQ ID NO 19
<211> LENGTH: 10
<212> TYPE: DNA
<213> ORGANISM: Artificial Sequence
<220> FEATURE:
<223> OTHER INFORMATION: Recombinant ExoN1

<400> SEQUENCE: 19
gaataacgta                                                             10

<210> SEQ ID NO 20
<211> LENGTH: 10
<212> TYPE: DNA
<213> ORGANISM: Bat Coronavirus

<400> SEQUENCE: 20
gaacgacgta                                                             10
```

METHODS, OLIGONUCLEOTIDES, AND KITS FOR DETECTION AND TREATMENT OF CORONAVIRUS

CROSS REFERENCE TO RELATED APPLICATIONS

This present application is the U.S. National Stage of International Application No. PCT/US2021/010015, filed Mar. 26, 2021, which claims the benefit of U.S. provisional patent application No. 63/000,476, filed Mar. 26, 2020, titled "METHODS FOR THE TREATMENT OF CORONAVIRUS INFECTION;" and U.S. provisional patent application No. 63/004,838, filed Apr. 3, 2020, titled "METHODS FOR THE DETECTION AND TREATMENT OF CORONAVIRUS;" the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6,909 byte ASCII (text) file named "SeqList" created on Feb. 17, 2023.

TECHNICAL FIELD

The present invention is directed to the field of detection and treatment of coronavirus, including, severe acute respiratory syndrome coronavirus 2 (SARS-CoV-2), which has been implicated in the pathogenesis of the disease COVID-19.

BACKGROUND

Seven coronaviruses that infect humans have been identified. Four are found to cause the common cold. The two alpha coronaviruses that are responsible for common cold symptoms are 229E (CoV-229E) and NL63 (CoV-NL63). The two beta coronaviruses that are responsible for common cold symptoms are OC43 (CoV-OC43) and HKU1 (CoV-HKU1). The other three coronaviruses cause more severe respiratory conditions. The first of which is SARS-CoV, which was responsible for a 2002-2003 outbreak of severe acute respiratory syndrome (SARS). The second of which is MERS-CoV, which caused outbreaks of Middle East Respiratory Syndrome (MERS) in 2012, 2015, and 2018. The third of which is SARS-CoV-2, which is the cause of the current pandemic of COVID-19.

COVID-19 was first reported in China in December 2019. Symptoms of COVID-19 is flu-like symptoms and can lead to pneumonia or more severe conditions. However, most people infected with the COVID-19 virus and develop symptoms will experience only mild to moderate respiratory illness and recover without requiring special treatment. Older people, and those with underlying medical problems like cardiovascular disease, diabetes, chronic respiratory disease, and cancer are more likely to develop serious illness. More than a year after the first reported case of COVID-19, there still remains no specific treatment for COVID-19.

Unlike most other respiratory disease, COVID-19 is known to spread even from an asymptomatic infected person to a close contact. An estimated 40% of individuals with SARS-CoV-2 infection are asymptomatic. Accordingly, SARS-CoV-2 can easily quietly spread within the community. Identifying where SARS-CoV-2 infections are taking place in the community is key to slowing the spread of COVID-19. Unfortunately, limitations in identifying the infection resulted in COVID-19 being declared a pandemic by the World Health Organization. To date, the pandemic has yet to end, and SARS-CoV-2 continues to place public health and economic stresses on the world. Identification of the etiology of COVID-19 and related illnesses is important in order to understand risk factors, target surveillance, properly treat diagnosed COVID-19 patients, and to help limit additional outbreaks. Thus, detecting SARS-CoV-2 infection as early and as fast as possible with a sensitive, reliable test remains crucial for ending the COVID-19 pandemic.

Because all seven human coronaviruses cause respiratory symptoms with varying degrees of severity, it would also benefit public health if people with respiratory symptoms could be accurately and reliably diagnosed with a particular type of coronavirus infection. There is currently no specific treatment for coronavirus infections.

SUMMARY

A need exists for a rapid molecular assay to diagnose patients with suspected coronavirus infection, to aid in the diagnosis of more severe conditions like SARS, MERS, or COVID-19, and for future surveillance and epidemiology. The emergence and rapid spread of SARS-CoV-2 to numerous areas throughout the world, has necessitated preparedness and response in public health laboratories, as well as health care and other areas of society in general. The availability of specific and sensitive assays for the detection of the virus are essential for accurate diagnosis of cases, assessment of the extent of the outbreak, monitoring of intervention strategies and surveillance studies.

The disclosed oligonucleotides, methods, and kits can be used in an assay to detect the presence or absence of human and non-human coronaviruses in a biological sample and to aid in diagnosis of a subject as having coronavirus infection and related disease, for example COVID-19, thereby informing treatment decisions for the subject. The present invention identifies conserved 5'- and 3'-terminal regions in SARS-CoV-2 and across members of the Betacoronavirus lineage B. Notable genotypes unique to each of SARS-CoV-2, SARS-CoV, and bat CoVs were determined, and the high degree of conservation of the 5'- and 3'-terminal regions indicate functional roles, for example, long-range spatial interactions with viral and/or host molecules that are essential for viral replication.

Accordingly, in some aspects, the disclosure relates to oligonucleotides (having a 5' terminus and a 3' terminus) that recognize regions in the 3' terminal regions in the SARS-CoV-2 genome. In some embodiments, the nucleotide sequence of the oligonucleotide consists of 300 or less continuous nucleotides from a nucleotide sequence selected from the group consisting of: SEQ ID NO: 1, SEQ ID NO:2, SEQ ID NO:3, SEQ ID NO:4, and SEQ ID NO:5, or is a variant thereof. In other embodiments, the nucleotide sequence of the oligonucleotide consists of 150 or less continuous nucleotides from a nucleotide sequence selected from the group consisting of: SEQ ID NO: 1, SEQ ID NO:2, SEQ ID NO:3, SEQ ID NO:4, and SEQ ID NO:5, or is a variant thereof. In still other embodiments, the nucleotide sequence of the oligonucleotide consists of 40 or less continuous nucleotides from a nucleotide sequence selected from the group consisting of: SEQ ID NO: 1, SEQ ID NO:2, SEQ ID NO:3, SEQ ID NO:4, and SEQ ID NO:5, or is a variant thereof. In yet other embodiments, the nucleotide sequence of the oligonucleotide consists of 40 or less nucleotides and is complementary to a nucleotide sequence selected from the group consisting of: SEQ ID NO:1, SEQ ID NO:2, SEQ ID NO:3, SEQ ID NO:4, and SEQ ID NO:5, or is a variant thereof. In some aspects, the variant thereof has no more than 5 substitutions, deletions, or additions. In some embodiments, the oligonucleotide is modified with an internal spacer or a detectable label. In some embodiments, the 5' terminus is labeled with a fluorophore and the 3' terminus is complexed to a quencher of fluorescence of said fluorophore. In some aspects, the nucleotide sequence of the oligonucleotide further comprises a universal tail sequence.

In particular embodiments, the oligonucleotide for use in detecting severe acute SARS-CoV-2 in a biological has a nucleotide sequence comprising 40 or less nucleotides from SEQ ID NO: 1, or a variant thereof; a nucleotide sequence comprising 300 or less nucleotides from SEQ ID NO: 1, or a variant thereof; or the nucleotide sequence comprises 40 or less nucleotides from SEQ ID NO: 1 or a variant thereof.

The kits described herein comprises a primer pair and coronavirus detection reagents. The primer pair amplifies a region of a nucleotide sequence selected from the group consisting of: SEQ ID NO:1, SEQ ID NO:2, SEQ ID NO:3, SEQ ID NO:4, and SEQ ID NO:5, so the primer pair is capable of detecting coronavirus, if present, in the sample by amplification. Each primer of the primer pair consists of 60 or less nucleotides. For example, one primer of the primer pair comprises 40 or less continuous nucleotides of the sequence of SEQ ID NO:1, SEQ ID NO:2, SEQ ID NO:3, SEQ ID NO:4, and SEQ ID NO:5, or variant thereof. The nucleotide sequence of the other primer of the primer pair is complementary to 40 or less continuous nucleotides of the sequence of SEQ ID NO: 1, SEQ ID NO:2, SEQ ID NO:3, SEQ ID NO:4, and SEQ ID NO:5, or variant thereof. In some aspects, the nucleotide sequence of the variant has no more than 5 substitutions, deletions, or additions. In some embodiments, the at least one of the primers of the primer pair is modified with an internal spacer or a detectable label. In certain embodiments, the kit further comprises a probe modified with an internal spacer or detectable label. The probe hybridizes to a region of a nucleotide sequence selected from the group consisting of: SEQ ID NO:1, SEQ ID NO:2, SEQ ID NO: 3, SEQ ID NO:4, and SEQ ID NO:5, for example, a region of 300 or less continuous nucleotides of SEQ ID NO:1, SEQ ID NO:2, SEQ ID NO:3, SEQ ID NO:4, and SEQ ID NO:5. In some aspects, the probe is labeled with a fluorophore and a quencher of fluorescence of the fluorophore.

The kit may further comprise running buffer and a test strip. The test strip comprises filter paper and/or chitosan. The forward primer, the reverse primer, the detectably labeled probe, and the one or more PCR reagents may be lyophilized. The kit may further comprise an indication of a result that signifies the presence of coronavirus and an indication of a result that signifies the absence of coronavirus. The result may comprise a Ct value or a Cq value.

The methods described herein comprise mixing the biological sample in vitro with a primer pair that is capable of amplifying a coronavirus amplicon product, if the coronavirus polynucleotide is present in the biological sample, and amplifying the coronavirus amplicon product. The sequence of at least one primer of the primer pair comprises 40 or less continuous nucleotides from a nucleotide sequence selected from the group consisting of: SEQ ID NO:1, SEQ ID NO: 2, SEQ ID NO:3, SEQ ID NO:4, and SEQ ID NO:5, or is a variant thereof. In some implementations, the nucleotide sequence of the variant has no more than 5 substitutions, deletions, or additions when compared to the 40 or less continuous nucleotide region of SEQ ID NO: 1, SEQ ID NO:2, SEQ ID NO:5, or SEQ ID NO:6.

The method further comprises contacting the coronavirus amplicon product with a probe having a nucleotide sequence capable of hybridizing to the coronavirus amplicon product, the probe being modified with an internal spacer or detectable label, and detecting whether coronavirus polynucleotides are present in the biological sample by detecting the detectable label when the probe hybridizes to the coronavirus amplicon. In particular implementations, the amplicon product has a nucleotide sequence that consists essentially of 300 or less nucleotides from a nucleotide sequence selected from the group consisting of: SEQ ID NO:1, SEQ ID NO:2, SEQ ID NO:3, SEQ ID NO:4, and SEQ ID NO:5, or is a variant thereof. Thus, the probe has a nucleotide sequence that consists essentially of the amplicon product or 150 or less nucleotides of the amplicon product. In some aspects, the probe is labeled with a fluorophore and a quencher of fluorescence of the fluorophore. The nucleic acid amplification may comprise calculating a Ct value or a Cq value.

In some embodiments, the biological sample comprises a nasopharyngeal swab sample or sputum. In some aspects, the biological sample is from a human, for example a human suspected to have a coronavirus infection.

In particular embodiments of the methods, the sequence of at least one primer of the primer pair further comprises a universal tail sequence. Thus, the method further comprises adding an index to the nucleic acid amplification products using at least one indexing oligonucleotide. The at least one indexing oligonucleotide comprises a complementary sequence that recognizes the universal tail sequence. In some implementations, the method further analyzing the nucleic acid amplification products by sequencing the nucleic acid amplification products using next-generation sequencing.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE DRAWINGS

FIGS. 1A and 1B illustrate coronavirus family genome diversity and conserved features. The coronavirus family whole genome phylogeny with different genera and sublineages represented is provided on the left. Each row corresponds to a different coronavirus family member annotated with host, genus, collection location and year, and the isolate name. The columns on the right correspond to gene products (FIG. 1A) and UTR (FIG. 1B) features along the length of the coronavirus genomes with each feature normalized to the same column width. The color shading intensities indicate the degree of nucleotide and amino acid conservation (i.e., sequence identity) with respect to the SARS-COV-2 reference genome (NC_045512.2).

Figure 2C:
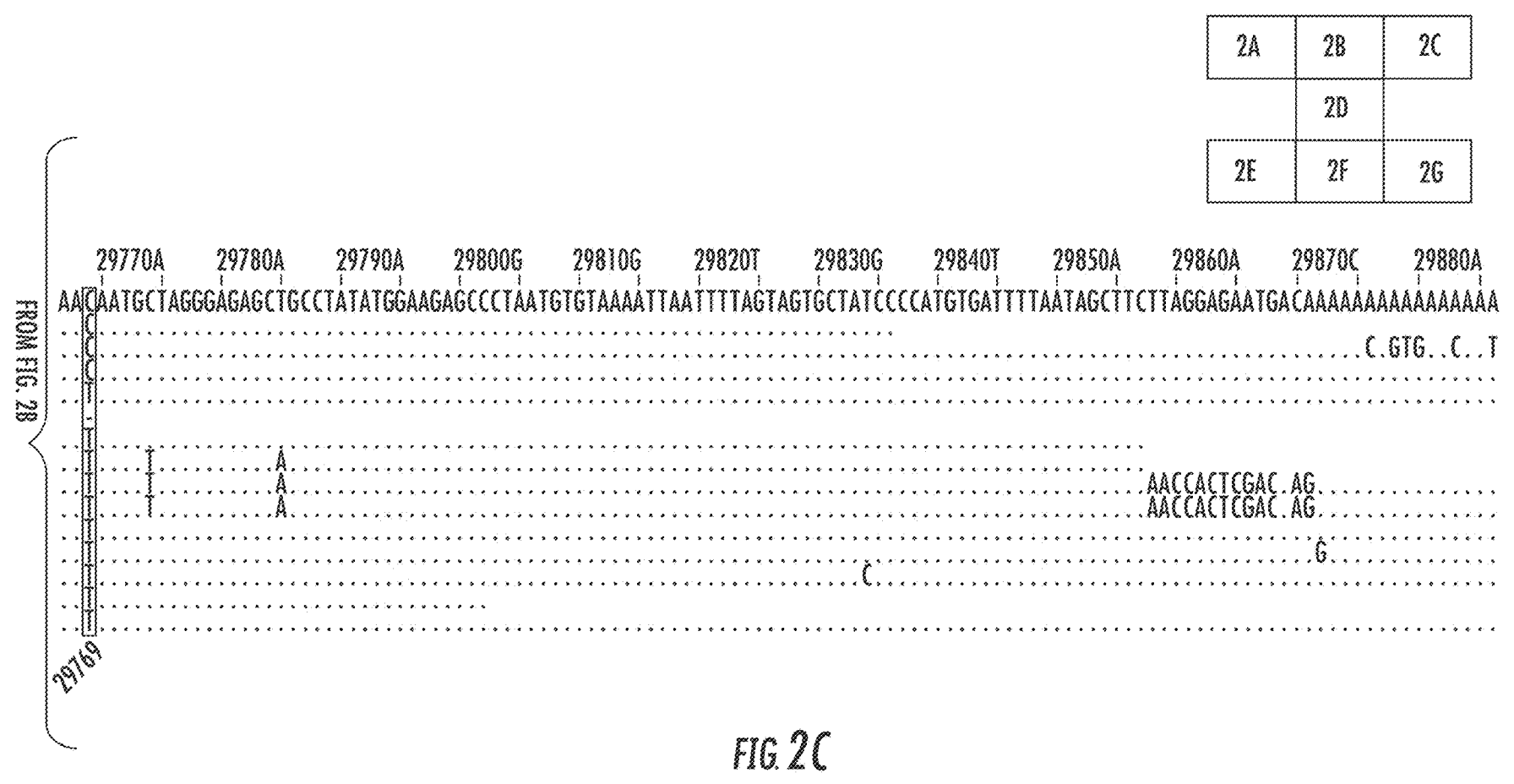

FIGS. 2A-2G illustrate UTR signatures of BetaCoV lineage B genomes. Variant positions in the SARSCOV-2 5'- and 3'-UTRs and their presence in related SARS-COV genomes (FIG. 2D). Base positions are depicted in their genomic locations for the 3'-UTR (FIGS. 2A-2C) and 5'-UTR (FIGS. 2E-2G) sequence coordinates. For each panel, the data tracks are: SNV frequency in SARS-COV-2 genomes based on 18 k GISAID genomes analyzed, SNV positions with >0.5% mutation frequency, UTR signature positions, conserved sequence motifs, predicted stem-loops, and predicted complementary base-pairing. The number of betaCoV genomes (#Genomes) carrying each unique signature is shown in a bar plot to the right with the following codings for host species: white, human; vertical line, bat; diagonal lines, laboratory; and black, civet. The 241C>T SNV is indicated by an asterisk) with an observed frequency of 70.2% (outside of the frequency scale shown). The 29553G>A SNV is upstream of the 3'-terminal with no ORF annotation showing moderately high mutation frequency at 1.42%. S2m: Coronavirus 3' stem-loop II-like motif, TRS: transcription regulatory sequence. the 3'-terminal with no ORF annotation showing moderately high mutation frequency at 1.42%. S2m: Coronavirus 3' stem-loop II-like motif, TRS: transcription regulatory sequence.

FIGS. 3A-3C illustrate SARS-CoV-2 single nucleotide variants (SNV) properties. FIG. 3A shows SNV counts and density (per kb feature length) across genes and UTRs. FIG. 3B depicts the SNV density shown by selected base change types: C>T/G>A, A>G/T>C, and G>T/C>A. A full set of SNV distribution across all 12 base change types is shown in Table 6. FIG. 3C depicts the amino acid mutation bias comparing expected (potential) and observed SNVs for each gene or UTR feature.

FIG. 4A is an LD plot of SNVs in the 9 major co-evolving variant groups identified based on 86 k GISAID genomes showing the squared coefficient of correlation (r2). FIG. 4B shows LD plots of individual coevolving variant groups.

FIGS. 6A-6C illustrate putative human microRNA interactions with the SARS-CoV-2 UTRs. FIG. 6A shows the predicted secondary structures of the 3'-UTR. FIG. 6B shows the predicted secondary structures of the 5'-UTR. Putative human microRNA binding sites with their orientations are shown ([A]: antisense; [S]: sense). Nucleotides corresponding to the UTR signatures are colored in red. Sequence features of unknown functions (octamer and palindrome) in the 3'-UTR, and the conserved element TRS in the 5'-UTR are shown in blue. The S2m motif is indicated by two inverted triangles. FIG. 6C shows the putative base-pairings between human miRNA hsa-miR-1307-3p and the SARS-CoV-2 3'-UTR. The base-pairings of miR-1307-3p against the H1N1 NS1 C112A mutant and the H1N1 NS1 wild type sequences were based on (30) and updated using bifold prediction.

DETAILED DESCRIPTION

Figure 2A:
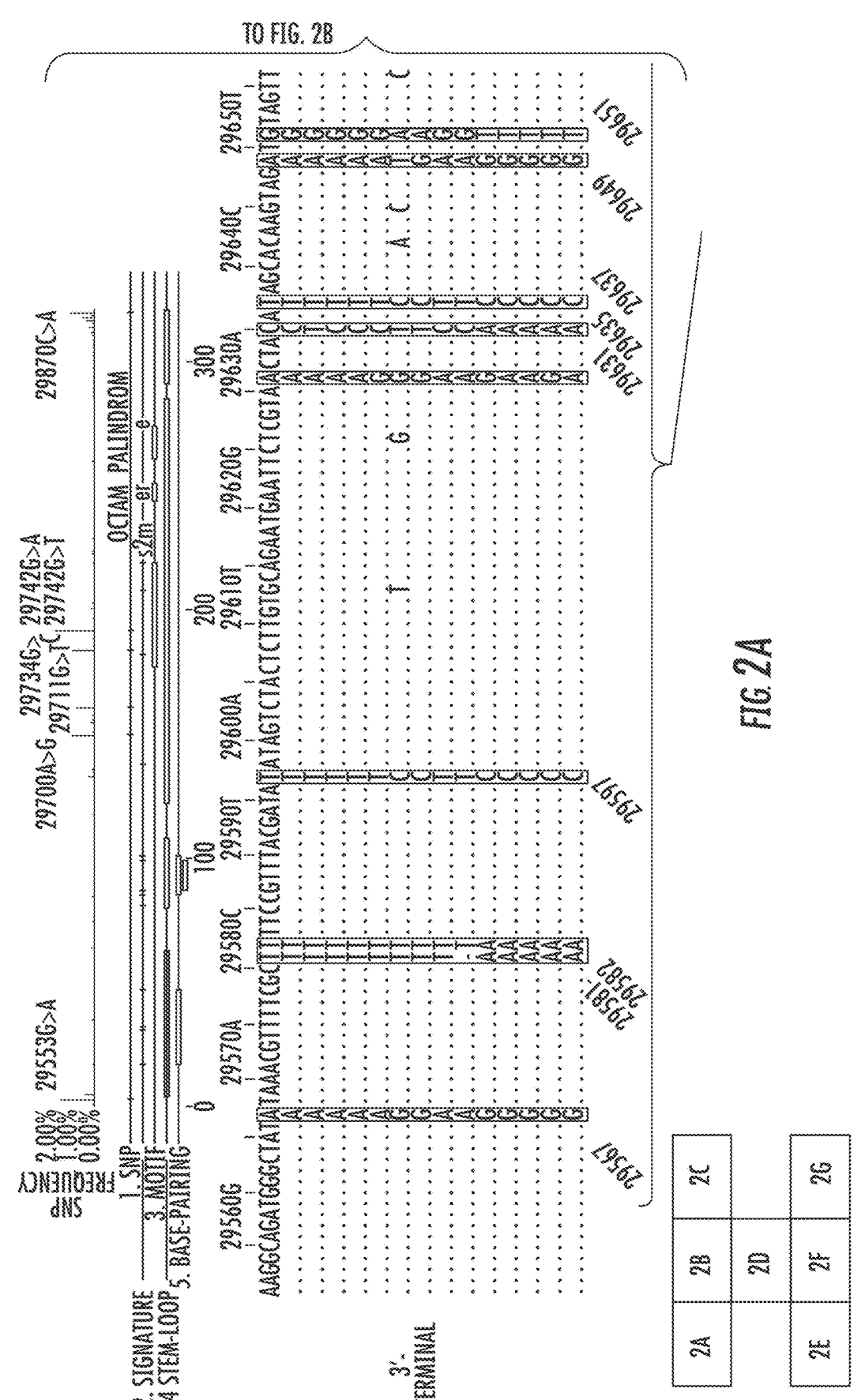
Figure 2B:
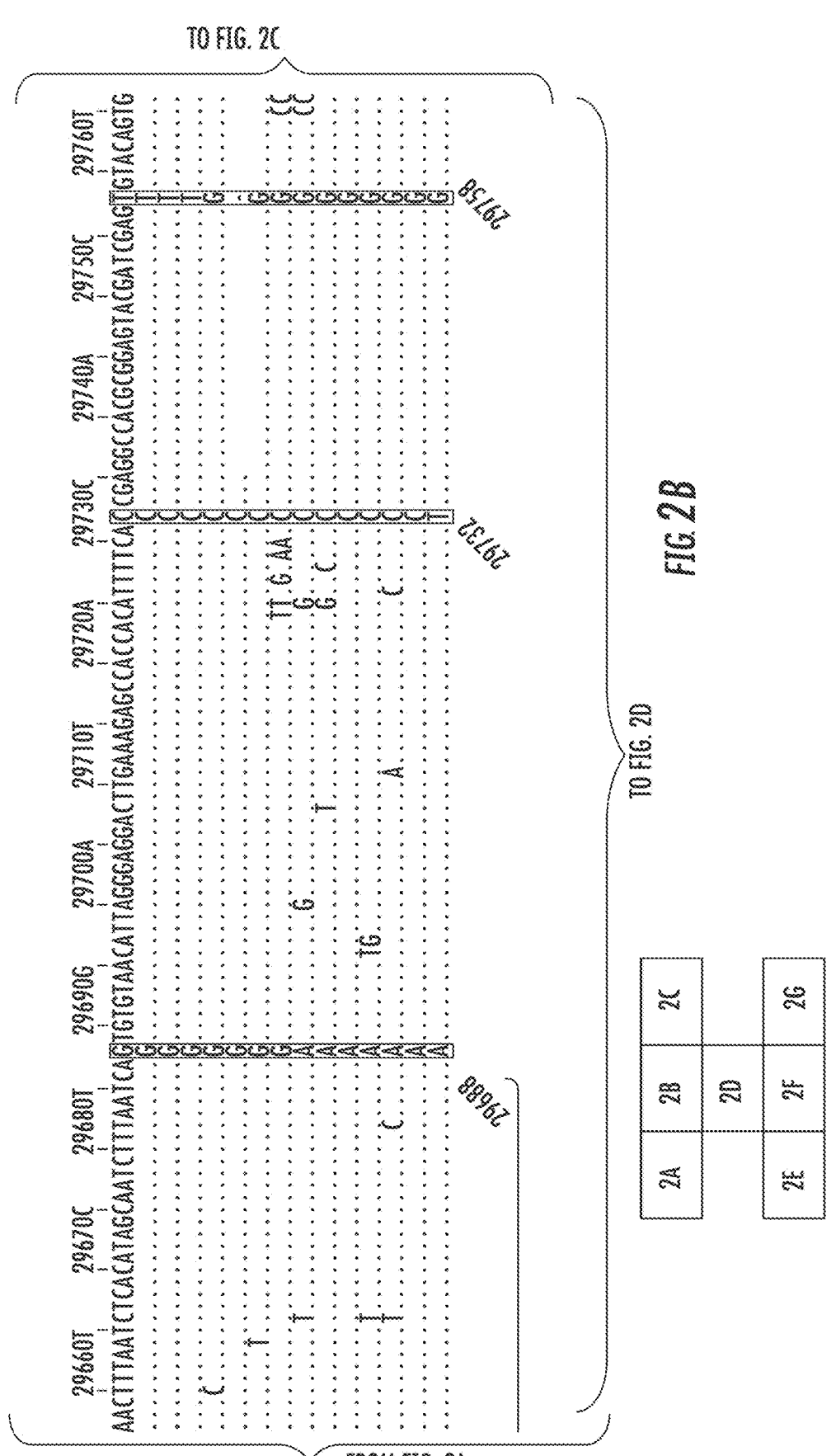
Figure 2D:
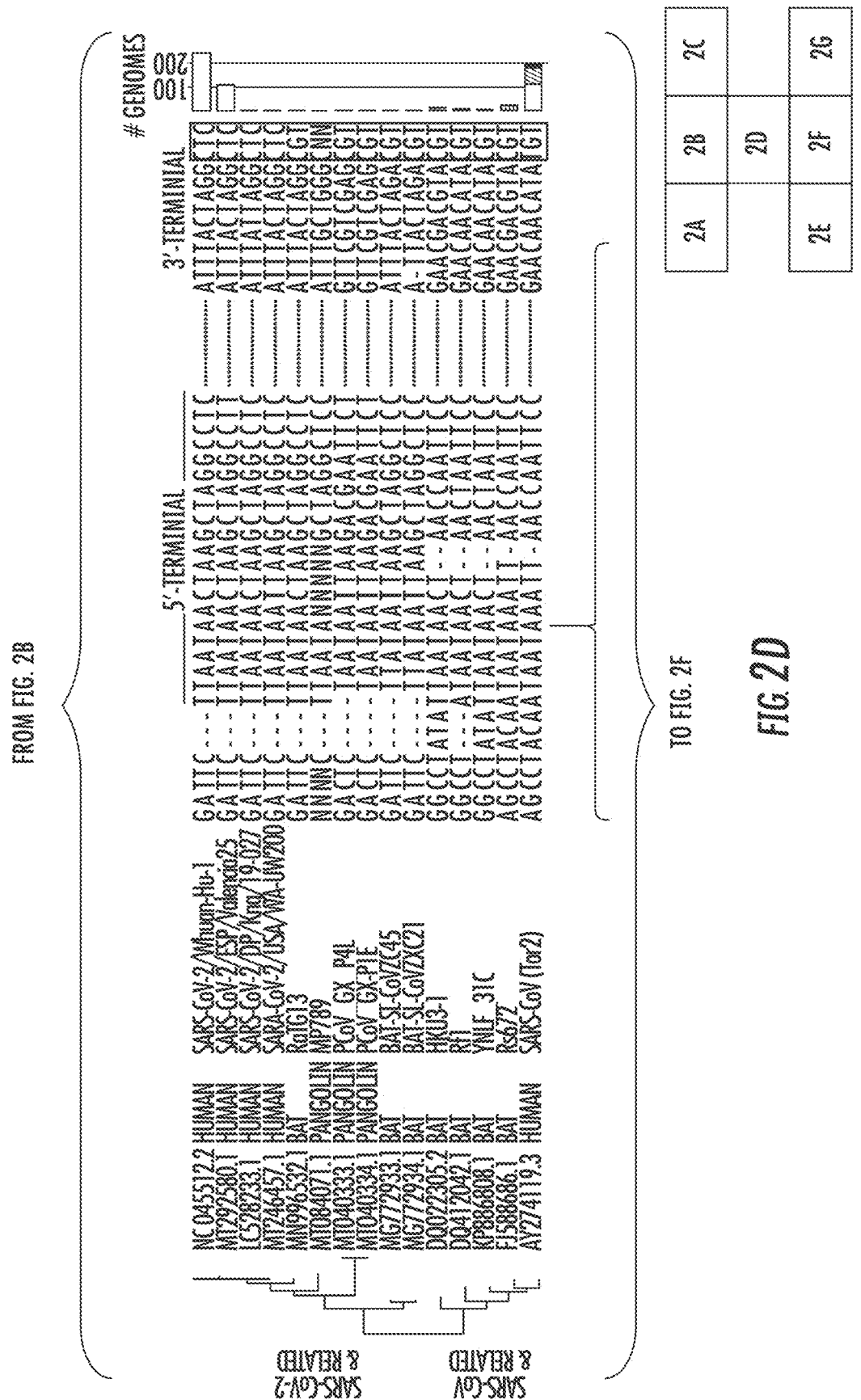
Figure 2E:
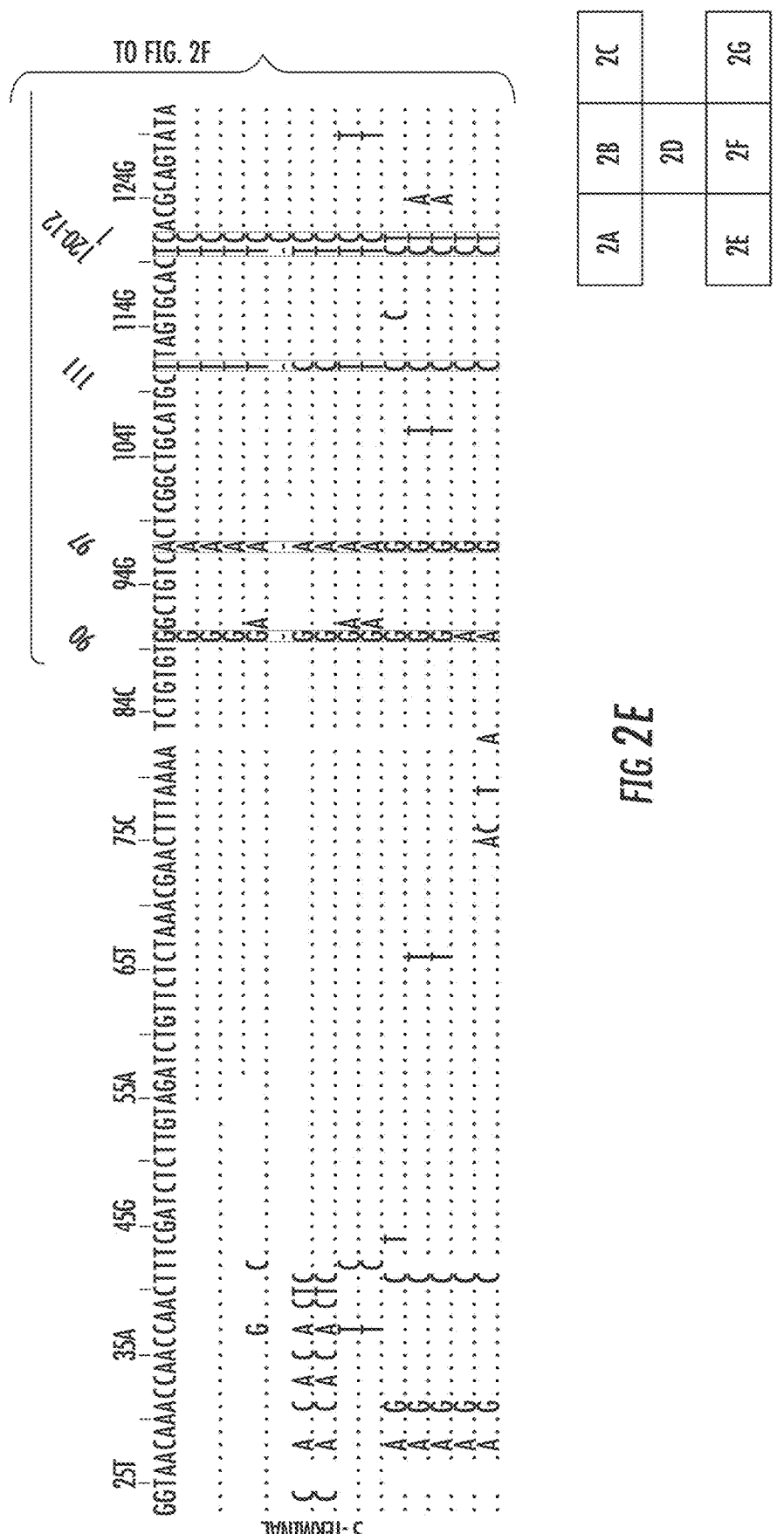
Figure 2F:
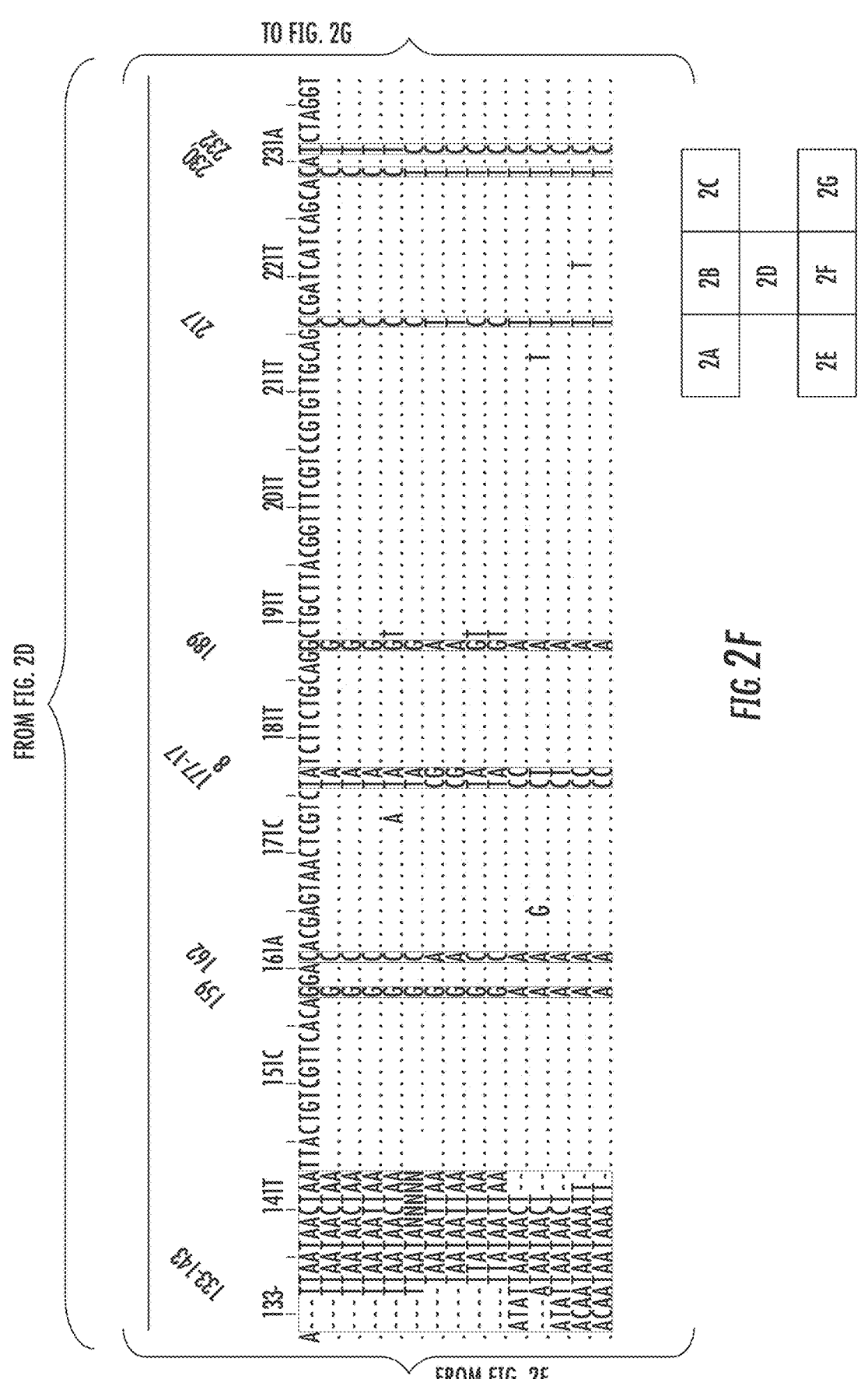
Figure 2G:
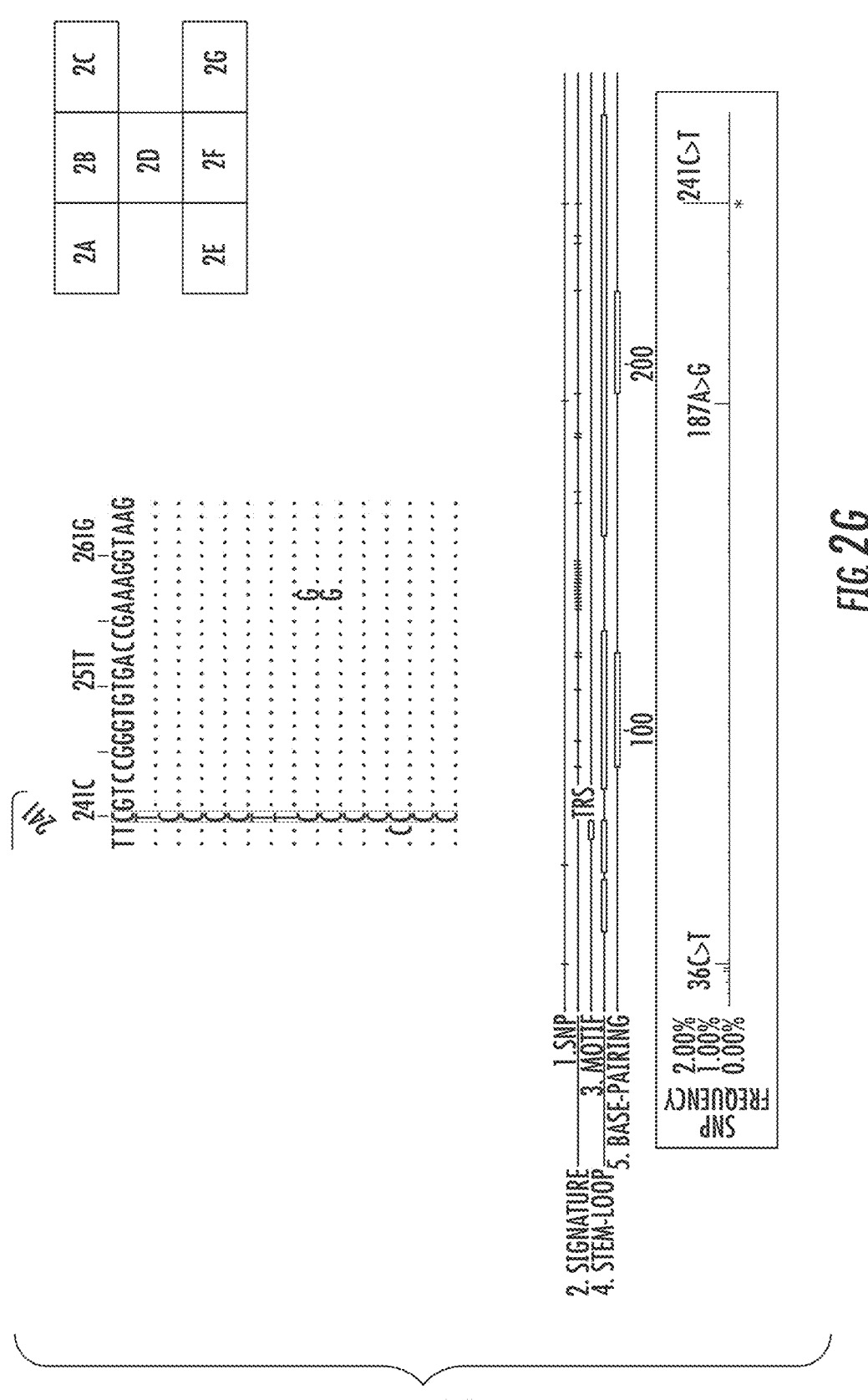

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

The present invention relates to methods and kits for assaying for the presence of coronavirus in a sample and to oligonucleotides, reagents and kits useful in such assays. In some embodiments, the methods, kits, and oligonucleotides are specific to a single coronavirus strain, such as SEQ ID NO:1 for detecting SARS-CoV-2. In other embodiments, primers and probes are specific to a plurality of coronavirus lineage B strains, such as SEQ ID NOS: 1-5, wherein the assays detects the presence of SARS-CoV-2, Bat CoV RaTG13, Pangolin-CoV, Bat-CoV-ZXC2, and Bat-CoV-ZC45. If the sample is from a human subject and the assay targets SEQ ID NOS: 1-5, a positive result indicates the presence of SARS-CoV-2 infection. This is because the Bat and Pangolin CoVs are clinically irrelevant in humans—they are not present in humans or do not infect humans. Thus, by targeting the 3'UTR sequence of the SARS-CoV-2 virus genome, the disclosed methods differentiates SARS-CoV-2 from other clinically relevant coronaviruses.

As used herein, the term "sample" (or specimen) may refer to any source in which coronavirus nucleic acids may be detectable. A sample may be derived from anywhere that a virus may be found including soil, air, water, solid surfaces (whether natural or artificial,) culture media, foodstuffs, and any interfaces between or combinations of these elements. Thus, a sample may be an environmental sample or a biological sample, such as a sample obtained from a subject. As used herein, a biological sample includes cells, tissues, and bodily fluids, such as: blood; derivatives and fractions of blood, such as plasma or serum; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; lymph fluid; ascites; serous fluid; pleural effusion; semen; amniotic fluid; stool; or hair. Samples may be collected by any method now known or yet to be disclosed, including swiping or swabbing an area or orifice, removal of a piece of tissue as in a biopsy, or any method known to collect bodily fluids. In some aspects, a biological sample includes nasal swab, nasopharyngeal swab, bronchial wash, or bronchioalveolar lavage fluid (BALF) from a subject. As used herein, the term "subject" refers includes humans or animals. Emphasis must be placed on the timely collection and appropriate handling of patient samples in order to increase the likelihood of detection of RNA viruses, in this case SARS-CoV-2 detection.

The methods and assays described herein are for the detection of SARS-CoV-2 in a sample in vitro. The disclosed methods and assays include polymerase chain reaction (PCR) test for the detection of nucleic acid from the coronavirus.

In some embodiments, the disclosed methods of detecting a coronavirus in a sample based on analyzing single nucleotide polymorphisms (SNPs) in the 3' untranslated region (UTR) of the coronavirus genome. The methods comprise extracting nucleic acids from the sample; amplifying a 3' UTR of the coronavirus genome to produce an amplification product; and detecting in the amplification product the presence or absence of one or more SNPs, wherein the one or more SNPs correspond to a nucleotide position of the coronavirus genome selected from the group consisting of position 29567, position 29581, position 29582, position 29597, position 29631, position 29635, position 29637, position 29649, position 29651, position 29688, position 29732, position 29735, position 29758, and position 29769. For detecting the presence of SARS-CoV-2, in the sample when one or more SNPs are detected selected from the group consisting of, referring to SEQ ID NO:1: an A or G at position 29567, a T or A at position 29581, a T or A at position 29582, a T or C at position 29597, an A or G at position 29631, a C or A at position 29635, a T or C at position 29637, an A or G at position 29649, a G or T at position 29651, a G or A at position 29688, a C or T at position 29732, an A or G at position 29735, a T or G at position 29758, and a C or T at position 29769. In certain implementations, the method further comprises receiving the sample from a subject and/or adding a plurality of primers to a mixture containing the sample.

In particular embodiments, the disclosed methods and assays include a real-time reverse transcription PCR (rRT-PCR) test for the qualitative detection of nucleic acid from the coronavirus. The disclosed coronavirus primer and probe sets are designed to detect RNA from the coronavirus in biological samples from patients, such as patients suspected of having COVID-19.

In some implementations, the biological sample is pretreated to extract RNA that may be present in the sample. Alternatively, the sample is evaluated without prior RNA extraction. For example, rRT-PCR assays of the present invention may be envisioned as involving multiple reaction steps:

(1) the reverse transcription of coronavirus RNA that may be present in the clinical sample that is to be evaluated for coronavirus presence;

(2) the PCR-mediated amplification of the coronavirus cDNA produced from such reverse transcription;

(3) the hybridization of coronavirus-specific probes to such amplification products;

(4) the double-strand-dependent 5'→3' exonuclease cleavage of the hybridized coronavirus-specific probes; and (5) the detection of the unquenched probe fluorophores signifying that the evaluated clinical sample contained coronavirus.

It will be understood that such steps may be conducted separately (for example, in two or more reaction chambers, or with reagents for the different steps being added at differing times, etc.). However, it is preferred that such steps are to be conducted within the same reaction chamber, and that all reagents needed for the rRT-PCR assays of the present invention are to be provided to the reaction chamber at the start of the assay. It will also be understood that although the PCR is the preferred method of amplifying SARS-CoV-2 cDNA produced via reverse transcription, other DNA amplification technologies could alternatively be employed.

Accordingly, in a preferred embodiment, the rRT-PCR assays of the present invention comprise incubating a clinical sample in the presence of a DNA polymerase, a reverse transcriptase, one or more pairs of coronavirus-specific primers, one or more coronavirus-specific probes (typically, at least one probe for each region being amplified by an employed pair of primers), deoxynucleotide triphosphates (dNTPs) and buffers. The conditions of the incubation are cycled to permit the reverse transcription of coronavirus RNA, the amplification of coronavirus cDNA, the hybridization of coronavirus-specific probes to such cDNA, the cleavage of the hybridized coronavirus-specific probes and the detection of unquenched probe fluorophores.

In various embodiments, the methods include detecting at least one coronavirus-specific amplicon in the sample using at least one primer pair which that is capable of amplifying a coronavirus amplicon product comprising a region of a nucleotide sequence selected from the group consisting of: SEQ ID NO:1, SEQ ID NO:2, SEQ ID NO:3, SEQ ID NO:4, and SEQ ID NO: 5. The presence of the coronavirus-specific amplicon indicates the presence of coronavirus in the sample. The absence of the coronavirus-specific amplicon indicates the absence of coronavirus from the sample.

The primer pair comprises a forward primer that hybridizes to a polynucleotide portion of a first strand of a DNA molecule and a reverse primer that hybridizes to a polynucleotide portion of a second (and complementary) strand of such DNA molecule. The forward and reverse primers will permit the amplification of 5' or 3' terminal regions of the coronavirus genome. The amplification of either of such targets alone is sufficient for the specific determination of coronavirus, for example SARS-CoV-2, presence in clinical samples. In some implementations, the sequence of at least one primer of the primer pair comprises 40 or less continuous nucleotides from a nucleotide sequence selected from the group consisting of: SEQ ID NO:1, SEQ ID NO:2, SEQ ID NO:3, SEQ ID NO:4, and SEQ ID NO:5, or is a variant thereof.

Thus, in particular implementations, the method comprises mixing the biological sample in vitro with a primer pair that is capable of amplifying a coronavirus amplicon product comprising a region of a nucleotide sequence selected from the group consisting of: SEQ ID NO:1, SEQ ID NO:2, SEQ ID NO:3, SEQ ID NO:4, and SEQ ID NO:5, if the coronavirus polynucleotide is present in the biological sample and then amplifying the coronavirus amplicon product. The method next comprises contacting the coronavirus amplicon product with a probe having a nucleotide sequence capable of hybridizing to the coronavirus amplicon product, the probe being modified with an internal spacer or detectable label; and detecting whether coronavirus polynucleotides are present in the biological sample by detecting the detectable label when the probe hybridizes to the coronavirus amplicon. In some embodiments, the method includes carrying out real-time PCR using one or more detectably labeled probes, thereby detecting the presence of a coronavirus in the subject. In some embodiments, the method includes carrying out real-time PCR using one or more detectably labeled probes, thereby detecting the presence of coronavirus in the subject.

The presence of such amplified molecules is preferably detected using probes that are capable of hybridizing to an oligonucleotide region present within the oligonucleotide that is amplified by the above-described coronavirus-specific primersSuch detection can be accomplished using any suitable method, e.g., molecular beacon probes, scorpion primer-probes, TaqMan® probes, etc. All of these methods employ an oligonucleotide that is labeled with a fluorophore and complexed to a quencher of the fluorescence of that fluorophore.

A wide variety of fluorophores and quenchers are known and are commercially available and may be used in accordance with the methods of the present invention. Preferred fluorophores include the fluorophores Biosearch Blue, Alexa488, FAM, Oregon Green, Rhodamine Green-X, NBD-X, TET, Alexa430, BODIPY R6G-X, CAL Fluor Gold 540, JOE, Yakima Yellow, Alexa 532, VIC, HEX, and CAL Fluor Orange 560 (which have an excitation wavelength in the range of about 352-538 nm and an emission wavelength in the range of about 447-559 nm, and whose fluorescence can be quenched with the quencher BHQ1), or the fluorophores RBG, Alexa555, BODIPY 564/570, BODIPY TMR-X, Quasar 570, Cy3, Alexa 546, NED, TAMRA, Rhodamine Red-X, BODIPY 581/591, Redmond Red, CAL Fluor Red 590, Cy3.5, ROX, Alexa 568, CAL Fluor Red 610, BODIPY TR-X, Texas Red, CAL Fluor Red 635, Pulsar 650, Cy5, Quasar 670, CY5.5, Alexa 594, BODIPY 630/650-X, or Quasar 705 (which have an excitation wavelength in the range of about 524-690 nm and an emission wavelength in the range of about 557-705 nm, and whose fluorescence can be quenched with the quencher BHQ2). The preferred SARS-CoV-2-specific TaqMan probes of the present invention are labeled with either the fluorophore 2',7'-dimethoxy-4',5'-dichloro-6-carboxyfluorescein ("JOE") or the fluorophore 5(6)-carboxyfluorescein ("FAM") on their 5' termini. JOE is a xanthene fluorophore with an emission in yellow range (absorption wavelength of 520 nm; emission wavelength of 548 nm). FAM is a carboxyfluorescein molecule with an absorption wavelength of 495 nm and an emission wavelength of 517 nm; it is typically provided as a mixture of two isomers (5-FAM and 6-FAM). Quasar 670 is similar to cyanine dyes, and has an absorption wavelength of 647 nm and an emission wavelength of 670 nm.

The black hole quencher 1 ("BHQ1") is a preferred quencher for FAM and JOE fluorophores. BHQ1 quenches fluorescent signals of 480-580 nm and has an absorption maximum at 534 nm.

The black hole quencher 2 ("BHQ2") is a preferred quencher for Quasar 670. BHQ2 quenches fluorescent signals of 560-670 nm and has an absorption maximum at 579 nm.

JOE, FAM, Quasar 670, BHQ1 and BHQ2 are widely available commercially and are coupled to oligonucleotides using methods that are well known. Oligonucleotide probes of any desired sequence labeled may be obtained commercially already labeled with a desired fluorophore and complexed with a desired quencher.

As discussed above, the proximity of the quencher of a TaqMan® probe to the fluorophore of the probe results in a quenching of the fluorescent signal. Incubation of the probe in the presence of a double-strand-dependent 5'→3' exonuclease (such as the 5"→3" exonuclease activity of Taq polymerase) cleaves the probe when it has hybridized to a complementary target sequence, thus separating the fluorophore from the quencher and permitting the production of a detectable fluorescent signal.

Molecular beacon probes can alternatively be employed to detect amplified SARS-CoV-2 oligonucleotides in accordance with the present invention. Molecular beacon probes are also labeled with a fluorophore and complexed to a quencher. However, in such probes, the quenching of the fluorescence of the fluorophore only occurs when the quencher is directly adjacent to the fluorophore. Molecular beacon probes are thus designed to adopt a hairpin structure while free in solution (thus bringing the fluorescent dye and quencher into close proximity with one another). When a molecular beacon probe hybridizes to a target, the fluorophore is separated from the quencher, and the fluorescence of the fluorophore becomes detectable. Unlike TaqMan probes, molecular beacon probes are designed to remain intact during the amplification reaction, and must rebind to target in every cycle for signal measurement.

Scorpion primer-probes can alternatively be employed to detect amplified coronavirus oligonucleotides in accordance with the present invention. Scorpion primer-probes are also designed to adopt a hairpin structure while free in solution and are also labeled with a fluorophore at their 5' terminus and complexed to a quencher at their 3' terminus. Scorpion primer-probes differ from molecular beacon probes in that their 3'-end is attached to their 5'-end by a hexathylene glycol (HEG) blocker. Such attachment prevents the polymerase-mediated extension of the 3' terminus of the scorpion primer-probe. However, after the scorpion primer-probe has bound to its target DNA, the polymerase copies the sequence of nucleotides from its 3'-end. In the next denaturation step, the specific sequence of the scorpion primer-probe binds to the complementary region within the same strand of newly amplified DNA. This hybridization opens the hairpin structure and, as a result, separates the molecules fluorophore from its quencher and permits fluorescence to be detected.

In a preferred embodiment, the probes of the present invention are TaqMa® probes. As described above, such probes are labeled on their 5' termini with a fluorophore and are complexed on their 3' termini with a quencher of the fluorescence of that fluorophore. In order to simultaneously detect the amplification of two polynucleotide portions of coronavirus, two TaqMan probes are employed that have different fluorophores (with differing and distinguishable emission wavelengths); the employed quenchers may be the same or different. In one embodiment of the invention, the 5' terminus of the first probe is labeled with the fluorophore JOE, and the 3' terminus of such probe is complexed to the quencher BHQ1 and the 5' terminus of the second probe is labeled with the fluorophore FAM, and the 3' terminus of such probe is complexed to the quencher BHQ1. In an alternative embodiment, the 5' terminus of the first probe is labeled with the fluorophore FAM, and the 5' terminus of the second probe is labeled with the fluorophore JOE. The use of such two fluorophores permits both probes to be used in the same assay.

The rRT-PCR assay described herein comprises one or more pairs of primers that amplify regions in the 5'- and 3'-terminal regions of the coronavirus genome. In one embodiment, the assay comprises a first primer pair and probe targeting targets at least one sequence selected from the group consisting of: SEQ ID NO:1, SEQ ID NO:2, SEQ ID NO:3, SEQ ID NO:4, SEQ ID NO: 5, SEQ ID NO:6, SEQ ID NO:7, SEQ ID NO:8, SEQ ID NO:9, and SEQ ID NO:10. The methods of detecting coronavirus in a sample in vitro comprise mixing the biological sample in vitro with a primer pair that is capable of amplifying a region of a coronavirus polynucleotide selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, if the coronavirus polynucleotide is present in the biological sample, and amplifying the coronavirus amplicon product.

Oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 70 bp, 80 bp, 90 bp, 100 bp, 150 bp, 200 bp, 250 bp, 300 bp, 350 bp, 400 bp, 450 bp, 500 bp, or any size amplicon greater in size or therebetween. In particular embodiments, the amplicon has a nucleotide sequence that consists essentially of 300 or less nucleotides from a nucleotide sequence selected from the group consisting of: SEQ ID NO: 1, SEQ ID NO:2, SEQ ID NO:3, SEQ ID NO:4, and SEQ ID NO:5, or is a variant thereof. In certain embodiments, the amplicon product detected has a nucleotide sequence that consists essentially of 150 or less nucleotides from a nucleotide sequence selected from the group consisting of: SEQ ID NO:1, SEQ ID NO:2, SEQ ID NO:3, SEQ ID NO:4, and SEQ ID NO:5, or is a variant thereof.

The method further comprises contacting the coronavirus amplicon product with a probe having a nucleotide sequence capable of hybridizing to the coronavirus amplicon product, the probe being modified with an internal spacer or detectable label, and detecting whether coronavirus polynucleotides are present in the biological sample by detecting the detectable label when the probe hybridizes to the coronavirus amplicon.

In some aspects, the probe is labeled with a fluorophore and a quencher of fluorescence of the fluorophore. The nucleic acid amplification may comprise calculating a Ct value or a Cq value.

In some embodiments, the biological sample comprises a nasopharyngeal swab sample or sputum. In some aspects, the biological sample is from a human.

The preferred primers and probes described are designed for the specific detection of coronavirus. Thus, the invention encompasses oligonucleotides of less than 40 nucleotides in length with nucleotide sequences of these oligonucleotides consisting of, consisting essentially of, or are "variants" of such preferred primers and probes. Thus, these oligonucleotides have a 5' terminus and a 3' terminus and have a nucleotide sequence comprising 40 or less continuous nucleotides from a nucleotide sequence selected from the group consisting of: SEQ ID NO:1, SEQ ID NO: 2, SEQ ID NO:3, SEQ ID NO:4, and SEQ ID NO:5, or is a variant thereof. In some implementations, the nucleotide sequence of the variant has no more than 5 substitutions, deletions, or additions when compared to the nucleotide sequence of SEQ ID NO:1, SEQ ID NO:2, SEQ ID NO:5, or SEQ ID NO:6.

As used herein, an oligonucleotide is a "variant" of another oligonucleotide if it retains the function of such oligonucleotide (e.g., acting as a specific primer or probe), but:
  (1) lacks 1, 2, 3, 4, 5, 6, 7, 8, 9, or 10 nucleotides of the nucleotides of such primer or probe, or
  (2) lacks 1, 2, 3, 4, 5, 6, 7, 8, 9, or 10 of the 10 3' terminal nucleotides of such primer or probe, or
  (3) lacks 1, 2, 3, 4, 5, 6, 7, 8, 9, or 10 of the 10 5' terminal nucleotides of such primer or probe, or
  (4) has a sequence that differs from that of such primer or probe in having 1, 2, 3, 4, 5, 6, 7, 8, 9, 10 or more than 10 additional nucleotides, or
  (5) has a sequence that differs from that of such primer or probe in having 1, 2, 3, 4, 5, 6, 7, 8, 9, 10 or more than 10 substitution nucleotides in lieu of the nucleotides present in such primer or probe, or
  (6) possesses a combination of such (1)-(5).

In some aspects, the variant thereof has no more than 5 substitutions, deletions, or additions. In some embodiments, the oligonucleotide is modified with an internal spacer or a detectable label. In some embodiments, the 5' terminus is labeled with a fluorophore and the 3' terminus is complexed to a quencher of fluorescence of said fluorophore. In certain embodiments, the nucleotide sequence of the oligonucleotide further comprises a universal tail sequence.

The disclose also provides kits for detecting coronavirus in biological samples. A "kit," as used herein, refers to a combination of at least some items for performing a PCR assay for coronavirus detection, and more particularly coronavirus strain differentiation, and more particularly SAR-CoV-2 detection. Embodiments of kits may comprise one or more of the following reagents: at least one set of primers specific for coronavirus detection, at least one probe specific for coronavirus detection, internal positive control DNA to monitor presence of PCR inhibitors from various food and environmental sources, a baseline control, reagents for sample collection, reagents for isolating nucleic acid such as magnetic beads, spin columns, lysis buffers, proteases, reagents for PCR amplification such as a DNA polymerase or an enzymatically active mutant or variant thereof, reverse transcriptase, a DNA polymerase buffer, buffer containing dNTPs, deoxyribonucleotides dATP, dCTP, dGTP, or dTTP. In some embodiments, a probe is a TaqMan® probe. In certain kit embodiments, amplification primers are attached to a solid support such as a microarray. In some embodiments, a kit may include an internal control (for example, RNase P assay).

One or more kit components may be packaged in one or more container means. Kit container means may generally include at least one vial, test tube, flask, bottle, syringe or other packaging means, into which a component can be placed, and in some embodiments, suitably aliquoted. Where more than one component is included in a kit (they can be packaged together), the kit also will generally contain at least one second, third or other additional container into which the additional components can be separately placed.

However, various combinations of components can be packaged in a container means. Kits of the present teachings also will typically include reagent containers in close confinement for commercial sale. Such containers can include injection or blow-molded plastic containers into which the desired container means are retained. When the components of kits are provided in one and/or more liquid solutions, the liquid solution comprises an aqueous solution that can be a sterile aqueous solution.

In certain embodiments, at least one kit component is lyophilized and provided as dried powder(s). For example, primers and TaqMan® probes may be lyophilized. When reagents and/or components are provided as a dry powder, the powder can be reconstituted by the addition of a suitable solvent. In certain embodiments, a solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented. A kit may also contain an indication that links the output of the kit to a particular result. For example, an indication may be one or more sequences or that signify the identification of SARS-CoV-2. An indication may include a Ct value, wherein exceeding the Ct value indicates the presence or absence of an organism of interest. A kit may contain a positive control. A kit may contain a standard curve configured to quantify the amount of coronavirus nucleic acid present in a sample. An indication includes any guide that links the output of the kit to a particular result. The indication may be a level of fluorescence or radioactive decay, a value derived from a standard curve, or from a control, or any combination of these and other outputs. The indication may be printed on a writing that may be included in the kit or it may be posted on the Internet or embedded in a software package.

In particular embodiments, the kit comprises a primer pair and coronavirus detection reagents. The primer pair amplifies a region of a nucleotide sequence selected from the group consisting of: SEQ ID NO:1, SEQ ID NO:2, SEQ ID NO:3, SEQ ID NO:4, and SEQ ID NO:5; primer pair is capable of detecting coronavirus, if present, in the sample by amplification; and each primer of the primer pair consist of 40 or less nucleotides. In some aspects, the nucleotide sequence of the variant has no more than 5 substitutions, deletions, or additions when compared to a region of 40 or less continuous nucleotides in SEQ ID NO:1, SEQ ID NO:2, SEQ ID NO:3, SEQ ID NO: 4, or SEQ ID NO:5. In some embodiments, the at least one of the primers of the primer pair is modified with an internal spacer or a detectable label. In certain embodiments, the kit further comprises a probe modified with an internal spacer or detectable label. The probe hybridizes to an region of a nucleotide sequence selected from the group consisting of: SEQ ID NO:1, SEQ ID NO: 2, SEQ ID NO:3, SEQ ID NO:4, and SEQ ID NO:5. In some aspects, the probe is labeled with a fluorophore and a quencher of fluorescence of the fluorophore.

The kit may further comprise running buffer and a test strip. The test strip comprises filter paper and/or chitosan.

Also described herein are therapeutic treatment of a coronavirus infection. In one aspect, the therapeutic treatment of a coronavirus infection comprise the administration of one or more of the following compounds or constructs: an anti-sense oligonucleotide targeting at least one sequence selected from the group consisting of SEQ ID NOS: 11-14, an siRNA targeting at least one sequence selected from the group consisting of SEQ ID NOS: 1-10, a small molecule targeting an s2m domain structure encoded by at least one sequence selected from the group consisting of SEQ ID NOS: 1-10, another construct as described herein, or a combination thereof. The fact that the disclosed targets regions are highly conserved indicate that the inhibition of Region 1 and/or Region 2 modulates the activity of coronavirus.

A construct designed to disrupt an important functional structure of the virus may have anti-viral effect. As shown in the Examples, the identified signatures suggest that inhibition of Region 1 and/or Region 2 has the potential to have an anti-viral effect. Thus, Region 1 and Region 2 are therapeutic targets for treating coronavirus infection. The specific target sequences for an inhibitor may include SEQ ID NOS: 1-10 from Table 4. In various embodiments, an inhibitor of SARS-CoV-2 may be a small interfering RNA (siRNA) which targets a nucleic acid sequences from Region 1 or Region 2. The siRNA may target one or more sequences comprising at least one sequence selected from the group consisting of SEQ ID NOS: 1-10. A therapeutic treatment for a coronavirus infection may comprise of the administration of one or more of the siRNAs.

EXAMPLES

The present invention is further illustrated by the following examples that should not be construed as limiting. The contents of all references, patents, and published patent applications cited throughout this application are incorporated herein by reference in their entirety for all purposes.

1. Materials and Methods a. Coronavirus Family Sequence Conservation Analysis The SARS-CoV-2 NCBI RefSeq genome (NC_045512.2) was used as the reference. For gene-by-gene analysis, each of 28 annotated genomic features (ORFs, processed peptides, and UTRs) of SARS-CoV-2 was searched against the 109 representative CoV genomes collected from four genera (alpha, beta, gamma, and delta) (Table 1) using NCBI BLAST+ (blastn and tblastx; v2.9.0) with an E-value threshold of 1e-3. The MSA of the 109 CoV family genome sequences was performed using Clustal Omega (v1.2.4). The maximum likelihood phylogeny tree was constructed using RAxML (v8.2.11) with 100 bootstraps under the GTRGAMMA model (2). The tree was visualized using iTOL.

b. SARS-CoV-2 Genomic Terminal Sequences

In the context of the studies described herein, the 5'-terminal (1 to 265 nt) corresponded to the annotated 5'-UTR. The 3'-terminal (29,558 to 29,903 nt), which was also denoted as 3'-UTR, corresponded to the annotated ORF10 and 3'-UTR of the SARS-CoV-2 reference genome (NC_045512.2).

c. Collection of betaCoV Lineage B Genomes and UTR Analysis

A total of 693 betaCoV genome sequences were initially collected from the NCBI Nucleotide database (nt database, as of Apr. 15, 2020, see Table 2). Genome sequences were collected using the entire SARS-CoV-2 genome sequence as the query for blastn search and requiring that most of the query sequence length and both UTR regions were aligned sufficiently for sequence comparison (i.e. at least 85% of query sequence is covered; an alignment starting from 130 or smaller nt position exists; and an alignment ending at 29700 nt or higher nt position exists). An MSA was performed on the collected 693 genome sequences including SARS-CoV-2 reference genome using Clustal Omega (v1.2.4). For the 3'- and 5'-UTR regions, variable positions were defined as any positions where 5% or more genomes showed nucleotide differences from the reference (excluding ambiguous nucleotides such as Ns). Positions near either end of the genome (i.e. <87 nt or >29806 nt) were excluded since over 1% of the genomes do not have aligned sequences and therefore the MSA may not be of high quality. Finally, after filtering out the genomes having ambiguous nucleotides on the defined variable positions on UTRs, 620 genomes were used as the final genome set for UTR signature analysis. Note that a pangolin CoV (MT084071.1) was included albeit having ambiguous nucleotides because it appeared to be one of likely close relatives of SARS-CoV-2 and also carried a unique UTR signature.

d. Prediction of UTR Secondary Structure

RNA secondary structure prediction was performed using the RNAfold web server with the default basic option to calculate "minimum free energy (MFE) and partition function". The predicted SARS-CoV-2 5'- and 3'-UTR structures previously reported were used to adjust the prediction.

e. SARS-CoV-2 Variant Analysis

A total of 34,217 SARS-CoV-2 genome sequences and their associated metadata were obtained from the GISAID on May 29, 2020. A data sanitization and filtering step was performed which included: removing gaps (dash and space characters), filtering out genomes from non-human host, and keeping only high-quality genomes (i.e. requiring a genome to be longer than 29 kb, and containing less than 1% Ns and no other ambiguous nucleotides such as B and W). Each of the remaining 18,599 high-quality genomes was aligned with the reference genome to identify variants using the nucmer and show-snps functions of the MUMmer package (v3.23). Sequence variants identified within the poly-A tail or near either end of sequence (within 10 nt from either end) were ignored. In addition, an MSA of the 18,599 genomes was built using MAFFT (v6.861b), which was used for independent validations of major mutation positions. For each sequence variant, the mutation effects on gene products (i.e. genic location and amino acid change if applicable) was analyzed using in-house scripts. The functional impact of amino acid substitutions and indels were predicted using PROVEAN. Linkage disequilibrium (LD) analysis was performed to identify co-evolving variants among SNVs with frequency of 0.1% or higher using Tagger implemented in Haploview (v4.2). Non-biallelic sites needed to be excluded from the LD analysis, and a set of 140 genomes with rare mutations on the major mutable sites, causing the sites to become non-biallelic, were also excluded.

The same analyses were repeated using an up-to-date (as of 5 Oct. 2020) data set with 135,500 genomes. After the same filtering steps, 86,450 genomes were included for the analyses, and the new findings in the coevolving variants group analysis were also reported.

f. Protein-Coding SNV Analysis

Each of the identified protein-coding SNVs was analyzed to determine its amino acid consequence (missense/synonymous/nonsense) using in-house scripts. For the estimation of amino acid consequences under the assumption of random mutations (i.e. to enumerate all potential SNVs given the sequence context of the SARS-CoV-2 genome), all 3 possible SNVs on every nucleotide position on all coding sequences from the start codon to the last codon before stop codon were included in the analysisd.

g. Identification of Putatively Interacting Human microRNAs

The UTR sequences of SARS-CoV-2 and SARS-CoV were used to search against the miRBase mature RNA sequences (Release 22.1) using blastn with the following parameters set for short sequences: "-penalty-4-reward 5-gapopen 25-gapextend 10-dust no-soft_masking false." For cross-species conservation analysis in other organisms, we searched the miRBase database requiring 18 or more bases matched with 100% sequence identity.

h. Statistical Analysis

To test for the significance of the G>T mutation bias toward the 3'-end of the genome, the proportion of G>T mutations out of summed gene lengths was compared between ORF1ab (60 mutations out of 21,326 nt) and the remaining ORFs (66 mutations out of 7,974 nt) using the Fisher's exact test implemented in fisher.test( ) function in the R stats package (v3.6.1).

i. Computing Systems

The Zenith computing system housed in Dell Technologies' High Performance Computing and Artificial Intelligence Lab in Austin, Texas was utilized to carry out much of the work. Zenith is a TOP500-class system based on a liquid and air-cooled scalable Intel systems framework that exploits over 400 servers as part of a Xeon Cascade computing lake, capable of over 1 petaflop peak performance. The system also include ~2 petabytes of Lustre, Isilon F800 and NSS storage that was used to enable local large-scale sequence similarity searches after obtaining sequence data from available sources (see above sections on data sources).

2. Coronavirus UTRs Comprise Potential Targets for Diagnostics and Antivirals Human coronaviruses are single-stranded RNA viruses and are evolutionarily related to other coronaviruses, such as bat and rodent coronaviruses. A search for potential interactions involving elements in the SARS-CoV-2 genome was undertaken. Because the non-coding regions of viral genomes could play important roles during infection such as replication, translation, and interactions with host proteins, this analysis focused on investigating the 5'- and 3'-termini of the SARS-CoV-2 genome via sequence comparisons and phylogenetic analyses. A search was performed using GISAID data for phylogenetic signals in available coronavirus genomes. Table 3A shows that few mutations were observed in the current viral outbreak based on approximately 2,400 sequenced viral genomes.

TABLE 3A

Observed mutations in current COVID-19 outbreak.

| Variant | Region 1 | Region 2 | Count | % | Notes |
|---|---|---|---|---|---|
| Reference | ATTTACTAGG (SEQ ID NO: 15) | CATC | 2406 | 98.85% | |
| 29567 | -TTTACTAGG (SEQ ID NO: 15) | CATC | 4 | 0.16% | 3 from Spain, 1 from Japan |
| 29567 | CTTTGCTAGG (SEQ ID NO: 15) | CATC | 1 | 0.04% | USA |
| 29635 | ATTTATTAGG (SEQ ID NO: 15) | CATC | 16 | 0.66% | 14 from Japan, 2 from USA |
| 29688 | ATTTACTAGT (SEQ ID NO: 15) | CATC | 1 | 0.04% | USA |
| 29732 | ATTTACTAGG (SEQ ID NO: 15) | TATC | 2 | 0.08% | Australia, China |
| 29732, 29635 | ATTTACTAGG (SEQ ID NO: 15) | GCTC | 1 | 0.04% | USA |
| 29758 | ATTTACTAGG (SEQ ID NO: 15) | CA-C | 2 | 0.08% | Australia, China |
| 29769 | ATTTACTAGG (SEQ ID NO: 15) | CATT | 1 | 0.04% | Ireland |

To identify conserved and potentially functional features in the CoV family, Coronaviridae, each of the annotated genes and UTR features of the SARS-CoV-2 reference genome (NC_045512.2) was compared against 109 selected CoV family genomes (Table 1). The SARS-CoV-2 reference isolate carries 26 processed peptides and open reading frames (ORFs), as well as 2 UTRs based on NCBI RefSeq annotation. The CoV family genomes studied were collected from four coronavirus genera (alpha, beta, gamma, and delta) including seven human CoVs (SARS-CoV-2, SARS-CoV, MERS, OC43, HKU1, 229E, and NL63), a number of mammalian CoVs (e.g. bats, pigs, pangolins, ferrets, civets), as well as avian CoVs (e.g. chicken, fowls). The SARS-CoV-2 sequence features were identified from searches against the CoV family genome sequences assuming both nucleotide and amino acid sequences using BLAST, independently of any CoV family genome annotation (FIG. 1).

The functional element-based conservation analysis results suggested that the 28 total genomic features (i.e., 26 processed peptides and ORFs+2 UTRs) can be broadly classified into two groups, those that were conserved across all CoV genera (cross-CoV feature group) and those that were conserved only within the betaCoV lineage B (beta-CoV lineage B-specific feature group), which includes human SARS-CoV-2 and SARS-CoV, and animal CoVs from bats, pangolins and civets. The cross-CoV feature group showed moderate levels of protein sequence identity across all genera and included nsp3-10, nsp12-16 (RNA-dependent RNA polymerase, helicase, 3'-to-5' exonuclease, endoRNAse, and 2'-O-ribose methyltransferase), and the structural proteins Spike(S), Membrane (M), and Nucleocapsid (N) (FIG. 1). The betaCoV lineage B-specific feature group mapped uniquely to the betaCoV lineage B, with no sequence similarity detected in other genera at the nucleotide or protein sequence levels. The betaCoV lineage B-specific feature group included non-structural proteins nsp2 and nsp11, accessory proteins ORF3a, ORF6, ORF7a, ORF7b, ORF8, ORF10, the structural Envelope (E) protein, and the 5'- and 3'-UTRs (FIG. 1). Among these, the five most conserved features between SARS-CoV-2 and the betaCoV lineage B isolates in descending order of average nucleotide sequence identity were the 3'-UTR, the E gene, ORF10, the 5'-UTR, and nsp10 at 97.4, 95.1, 93.8, 91.1, and 89.7%, respectively. A short stretch (~30 nt) of the SARS-CoV-2 3'-UTR also shared high sequence identities with specific groups of deltaCoVs (from pigs and birds; 97%) and gammaCoVs (from chicken and fowls; 94%). Taken together, these results showed that the nucleotide sequence of both genomic terminals (3'-UTR and 5'-UTR) are exceptionally conserved and unique within the betaCoV lineage B isolates, and therefore suggests they are of functional significance for SARS-CoV-2.

To investigate the extent of sequence conservation within the genomic terminals of SARS-CoV-2 and related isolates, a multiple sequence alignment (MSA) analysis was performed on 620 near-full-length betaCoV lineage B genomes collected from the NCBI Nucleotide database, which included 361 SARS-CoV-2, 113 SARS-CoV, 75 animal CoVs (e.g. bats, pangolins, civets), and 71 laboratory isolates (Table 2). The 5'-UTR (SARS-CoV-2, 1 to 265 nt) was defined as the 5'-terminal, and both ORF10 and the 3'-UTR together (29558 to 29903 nt) were used for the 3'-terminal analysis. ORF10 was included in the 3'-terminal analysis because ORF10 was a predicted ORF immediately upstream of the 3'-UTR but no ORF10 expression was detected as reported in a comprehensive SARS-CoV-2 transcriptome analysis. Hereinafter, all genomic coordinates follow the SARS-CoV-2 reference isolate (NC_045512.2) unless otherwise noted.

The MSA analysis of the 3'- and 5'-UTR revealed near-perfect sequence identity of the regions across the betaCoV genomes. Across the nucleotide positions where most genomes (>99%) have sequence alignments (i.e., ignoring positions near both ends of genome where many genomes do not have sequences), 94% of the 3'-UTR positions (234 out of 249) and 84% of the 5'-UTR positions (151 out of 179) shared identical nucleotides amongst 99% of the genomes aligned. Within these conserved regions, a high level of nucleotide diversity was observed at specific positions across the sequence alignments, with 13 and 25 hypervariable positions identified in the 3'- and 5'-UTR, respectively (FIG. 2). These 38 positions altogether showed distinct nucleotide profiles for sub-clades of the betaCoV genomes and are herein referred to as the UTR 'signatures.' A total of major 15 UTR signatures and their frequency distribution were determined from the 620 betaCoV genomes (FIG. 2).

Based on nucleotide identities, the UTR signatures could be clustered into two distinct groups represented by the SARS-CoV-2 (Wuhan-Hu-1) and SARS-CoV (Tor2) isolates respectively, which harbored 76% non-identical nucleotides (29 out of 38 positions at the UTR signature positions). The UTR signature of the SARS-CoV-2 clade was shared by bat CoV isolates (RaTG13, ZC45, and ZXC21) and pangolin CoV isolates (MP789, GX-P4L, and GX-P1E); and that of the SARS-CoV clade was shared by a different group of bat CoVs (HKU3-1, Rf1, YNLF_31C, and Rs672) (FIG. 2). In particular at the 3' end of the genome, a ~300 bp 3'-UTR was identified with lineage-specific sequence patterns (or signatures) across several coronavirus genomes.

Table 3B shows the sequence signatures for Regions 1 and 2. The Region 1 signature is defined by 10 nucleotides at positions 29567, 29581, 29582, 29597, 29631, 29635, 29637, 29649, 29651, and 29688. The Region 2 signature is defined by four (4) nucleotides at positions 29732, 29735, 29758, and 29769.

TABLE 3B

Sequence signatures

| Virus | Accession No. | Region 1 | Region 2 |
|---|---|---|---|
| SARS-CoV-2 [reference] | NC_045512.2 | ATTTACTAGG (SEQ ID NO: 15) | CATC |
| Bat CoV RaTG13 | MN996532.1 | ATTTACTAGG (SEQ ID NO: 15) | CAGT |
| Pangolin-CoV | MT084071.1 | ATTTGCTAGG (SEQ ID NO: 15) | CA-- |
| Bat-CoV-ZXC2 | MG772934.1 | A-TTACTAGA (SEQ ID NO: 16) | CAGT |
| Bat-CoV-ZC45 | MG772933.1 | ATTTACTAGA (SEQ ID NO: 17) | CAGT |
| Human-SARS-Tor2(2003) | AY274119.3 | GAACAACGTA (SEQ ID NO: 18) | TAGT |
| Recombinant-ExoN1 | FJ882928.1 | GAATAACGTA (SEQ ID NO: 19) | TAGT |
| Bat-CoV-HKU3-1 | DQ022305.2 | GAACGACGTA (SEQ ID NO: 20) | CAGT |
| Chicken-IBV | MN512438.1 | ---------- | CGG- |
| Chicken-IBV | MK581208.1 | ---------- | CAG- |

Overlaying the UTR signatures with predicted RNA secondary structures revealed that a majority of the signature positions (71%; 27 out of 38) were located on stem-loop structures, and that 10 positions were involved in complementary base-pairings. Interestingly, it was noted that the last three positions (29732, 29758, 29769 nt) of the 3'-UTR signature carried distinct nucleotide combinations for each group of the SARS-CoV-2 ('CTC'), SARS-CoV ('TGT'), and the bat CoVs ('CGT') isolates (FIG. 2). Notably, these three positions overlapped with a conserved RNA motif S2m (Coronavirus 3' stem-loop II-like motif, Rfam RF00164) previously identified in coronavirus and astrovirus. In this analysis, the highly conserved S2m RNA element was also detectable using nucleotide searches among avian and animal CoVs belonging to the gamma and delta genera (FIG. 1).

Table 4 shows the DNA sequences for Regions 1 and 2 from representative coronavirus genomes. SEQ ID NOS.

1-10 include signature Regions 1 and/or 2 which are highly conserved across various coronaviruses. Region 1 spans ORF10, and Region 2 spans a conserved s2m domain (scc FIG. 6A). Referring to the sequences in Table 4, SEQ ID NO:1 has a start-end position from 29,558 to 29,903. SEQ ID NOS: 2-8 have a start position of 29,558. SEQ ID NOS 9 and 10 have a start position of 29,372. Region 1 is shown for the various coronaviruses in Table 4 at positions 29,558 to 29,731. Region 2 is shown for the various coronaviruses in Table 4 starting at position 29,732.

TABLE 4

Examples of Coronavirus Sequences
Carrying Signatures in Regions 1 and 2

| Virus | Accession No. | Sequence |
|---|---|---|
| SARS-CoV-2 [reference genome sequence] | NC_045512.2 | ATGGGCTATATAAACGTTTTCGCTTTTCCGTTTACGAT ATATAGTCTACTCTTGTGCAGAATGAATTCTCGTAACT ACATAGCACAAGTAGATGTAGTTAACTTTAATCTCACA TAGCAATCTTTAATCAGTGTGTAACATTAGGGAGGACT TGAAAGAGCCACCACATTTTCACCGAGGCCACGCGGA GTACGATCGAGTGTACAGTGAACAATGCTAGGGAGAG CTGCCTATATGGAAGAGCCCTAATGTGTAAAATTAATT TTAGTAGTGCTATCCCCATGTGATTTTAATAGCTTCTTA GGAGAATGACAAAAAAAAAAAAAAAAAAAAAAAAAA AAAAAAA (SEQ ID NO: 1) |
| Bat CoV RaTG13 | MN996532.1 | ATGGGCTATATAAACGTTTTCGCTTTTCCGTTTACGAT ATATAGTCTACTCTTGTGCAGAATGAATTCTCGTAACT ACATAGCACAAGTAGATGTAGTTAACCTTAATCTCACA TAGCAATCTTTAATCAGTGTGTAACATTAGGGAGGACT TGAAAGAGCCACCACATTTTCACCGAGGCCACGCGGA GTACGATCGAGGGTACAGTGAATAATGCTAGGGAGAG CTGCCTATATGGAAGAGCCCTAATGTGTAAAATTAATT TTAGTAGTGCTATCCCATGTGATTTTAATAGCTTCTTAG GAGAATGACAAAAAAAAAAAAAAAAAAAA--------- ---- (SEQ ID NO: 2) |
| Pangolin-CoV | MT084071.1 | ATGGGCTATATAAACGTTTTCGCTTTTCCGTTTACGAT ATATAGTCTACTCTTGTGCAGAATGAATTCTCGTAGCT ACATAGCACAAGTAGATGTAGTTAACTTTAATCTCACA TAGCAATCTTTAATCAGTGTGTAACATTAGGGAGGACT TGAAAGAGCCACCACATTTTCACCGA------------ --------------------------------------- --------------------------------------- --------------------------------------- --------------------------------------- ------------------- (SEQ ID NO: 3) |
| Bat-CoV-ZXC2 | MG772934.1 | ATGGGCTATATAAACGTTTTCGC-TTTCCGTTTACGATA TATAGTCTACTCTTGTGCAGAATGAATTCTCGTAACTA CATAGCACAAGTAGATGTAGTTAACTTTAATCTCACAT AGCAATCTTTAATCAATGTGTAACATTAGGGAGGATTT GAAAGAGCCACCACGTTCTCACCGAGGCCACGCGGAG TACGATCGAGGGTACAGTGAATAATGTTAGGGAGAGC AGCCTATATGGAAGAGCCCTAATGTGTAAAATTAATTT TAGTAGTGCTATCCCCATGTGATTTTAATAGCTTCA- ACCACTC-GACAAGAAAAAAAAAAAAAAAAAAAAAAA AAAA---- (SEQ ID NO: 4) |
| Bat-CoV-ZC45 | MG772933.1 | ATGGGCTATATAAACGTTTTCGCTTTTCCGTTTACGAT ATATAGTCTACTCTTGTGCAGAATGAATTCTCGTAACT ACATAGCACAAGTAGATGTAGTTAACTTTAATTTCACA TAGCAATCTTTAATCAATGTGTAACATTGGGGAGGACT TGAAAGAGCCACCACGTTTTCACCGAGGCCACGCGGA GTACGATCGAGGGTACAGCCAATAATGTTAGGGAGAG CAGCCTATATGGAAGAGCCCTAATGTGTAAAATTAATT TTAGTAGTGCTATCCCCATGTGATTTTAATAGCTTCA- ACCACTC-GACAAGAAAAAAAAAAAAAAAAAAAAAAA AAA---- (SEQ ID NO: 5) |
| Human-SARS- Tor2(2003) | AY274119.3 | ATGGGCTATGTAAACGTTTTCGCAATTCCGTTTACGAT ACATAGTCTACTCTTGTGCAGAATGAATTCTCGTAACT AAACAGCACAAGTAGGTTTAGTTAACTTTAATCTCACA TAGCAATCTTTAATCAATGTGTAACATTAGGGAGGACT TGAAAGAGCCACCACATTTTCATCGAGGCCACGCGGA GTACGATCGAGGGTACAGTGAATAATGCTAGGGAGAG CTGCCTATATGGAAGAGCCCTAATGTGTAAAATTAATT TTAGTAGTGCTATCCCCATGTGATTTTAATAGCTTCTTA GGAGAATGACAAAAAAAAAAAAAAAAAAAAAAAAA---- ----- (SEQ ID NO: 6) |

TABLE 4-continued

Examples of Coronavirus Sequences
Carrying Signatures in Regions 1 and 2

| Virus | Accession No. | Sequence |
|---|---|---|
| Recombinant-ExoN1 | FJ882928.1 | ATGGGCTATGTAAACGTTTTCGCAATTCCGTTTACGAT<br>ATATAGTCTACTCTTGTGCAGAATGAATTCTCGTAACT<br>AAACAGCACAAGTAGGTTTAGTTAACTTTAATCTCACA<br>TAGCAATCTTTAATCAATGTGTAACATTAGGGAGGACT<br>TGAAAGAGCCACCACATTTTCATCGAGGCCACGCGGA<br>GTACGATCGAGGGTACAGTGAATAATGCTAGGGAGAG<br>CTGCCTATATGGAAGAGCCCTAATGTGTAAAATTAATT<br>TTAGTAGTGCTATCCCCATGTGATTTTAA----------<br>---- (SEQ ID NO: 7) |
| Bat-CoV-HKU3-1 | DQ022305.2 | ATGGGCTATGTAAACGTTTTCGCAATTCCGTTTACGAT<br>ACATAGTCTACTCTTGTGCAGAATGAATTCTCGTAGCT<br>AAACAGCACAAGTAGGTTTAGTTAACTTTAATCTCACA<br>TAGCAATCTTTAATCAATGTGTAACATTAGGGAGGACT<br>TGAAAGAGCCACCACATTTTCACCGAGGCCACGCGGA<br>GTACGATCGAGGGTACAGTGAATAATGCTAGGGAGAG<br>CTGCCTATATGGAAGAGCCCTAATGTGTAAAATTAATT<br>TTAGTAGTGCTATCCCCATGTGATTTTAATAGCTTCTTA<br>GGAGAATGACAAAAAAAAAAAAAAAAAAAAAAAA----<br>----- (SEQ ID NO: 8) |
| Chicken-IBV | MN512438.1 | ----------------------------------------<br>----------------------------------------<br>----------------------------------------<br>----------------------------------------<br>----------------CCGGGGCCACGCGGAGTACGATC<br>GAGGGTACAG----------------------------<br>----------------------------------------<br>----------------------------------------<br>-------------------------------<br>(SEQ ID NO: 9) |
| Chicken-IBV | MK581208.1 | ----------------------------------------<br>----------------------------------------<br>----------------------------------------<br>----------------------------------------<br>----------------CCGAGGCCACGCGGAGTACGATC<br>GAGGGTACAG----------------------------<br>----------------------------------------<br>----------------------------------------<br>-------------------------------<br>(SEQ ID NO: 10) |

These results show that the 3'- and 5'-UTRs of SARS-CoV-2, SARS-CoV, and batCoV isolates carry unique signatures involving predicted RNA secondary structures with likely functional and/or regulatory roles. For example, the 3'UTR sequence (SEQ ID NO:1) is unique to the SARS-CoV-2 virus. The human SARS-CoV (2003) has ~10 mismatches, and the human MERS-CoV (2012) no similarity at the sequence level. Thus, SEQ ID NO:1 is a potential target for diagnosis of SARS-CoV-2, to aid in COVID-19 diagnosis, and to rule out other coronavirus infection.

Altogether, sequence analysis revealed a remarkable conservation of primary sequences and predicted secondary structures at the 5'- and 3'-terminal regions between SARS-CoV-2, SARS-CoV (2003), and a subgroup of bat CoVs all belonging to the Betacoronavirus lineage B. These terminal sequences were specific to lineage B. More precisely, with the exception of ORF1ab, the 5'- and 3'-terminal sequences, the structural genes (S, E, M, and N protein genes), and the remaining ORFs were unique to lineage B and shared no detectable nucleotide similarity (requiring >30% length coverage per gene) with other human coronavirus families such as CoV-MERS (Betacoronavirus lineage C), HCoV-OC43 (Betacoronavirus lineage A), or HCoV-NL63 (Alphacoronavirus).

3. Coronavirus UTRs are Conserved and Exhibit Distinct Variant Sites

To investigate SARS-CoV-2 genomic stability, genome-wide nucleotide variants amongst isolates collected from the ongoing global outbreak were analyzed. Single nucleotide variant (SNV) discovery was performed by pairwise whole genome alignments using Nucmer on 18,599 whole genome sequences available from the GISAID resource (as of May 29, 2020) (Table 5), and a set of stringent filtering criteria to identify high confidence SNVs. Variant analysis identified 87 variant (SNV) positions with frequencies >0.5% (or, equivalently, occurring in at least 93 genomes). Inspection of the UTR signature positions showed that 37 out of 38 positions were relatively stable within SARS-CoV-2 isolates with variants detected in <0.11% genomes (i.e., 20 isolates or fewer) (FIG. 2). One exception was the variant g.241C>T variant, which represented one of the signature positions and was originally discovered using 361 SARS-CoV-2 genomes in the betaCoV lineage B analysis above. In the expanded 18 k SARS-CoV-2 genome analysis, the g.241C>T variant was detected at a high prevalence of 70.2%. In addition, six variants were identified at five sites in the 3'-UTR (g.29700A>G, g.29711G>T, g.29734G>C, g.29742G>T, g.29742G>A, g.29870C>A) and three in the 5'-UTR (g.36C>T, g.187A>G, g.241C>T) (FIG. 2). Setting g.241C>T aside, the UTR variants were detected at a low frequency, between 0.62 and 1.05%. All UTR variants were located on predicted stem-loop structures with the exception of g.36C>T in the 5'-UTR. It was noted that the 29742 position was located within the conserved RNA motif S2m, and carried two alternate alleles, making it a triallelic site (FIG. 2). The alternate allele g.29742G>T was observed with a frequency of 1.05%, and the second alternate allele g.29742G>A at a frequency of 0.67%. Based on whole genome phylogeny analysis, the g.29742G>T and g.29742G>A variants appeared to have arisen in two distinct clades: the g.29742G>T variant was predominantly found in Asia (43% of G>T isolates), and g.29742G>A almost equally split between Asia and North America (40.0 and 39.5% respectively of G>A isolates).

Figures 3A, 3B:
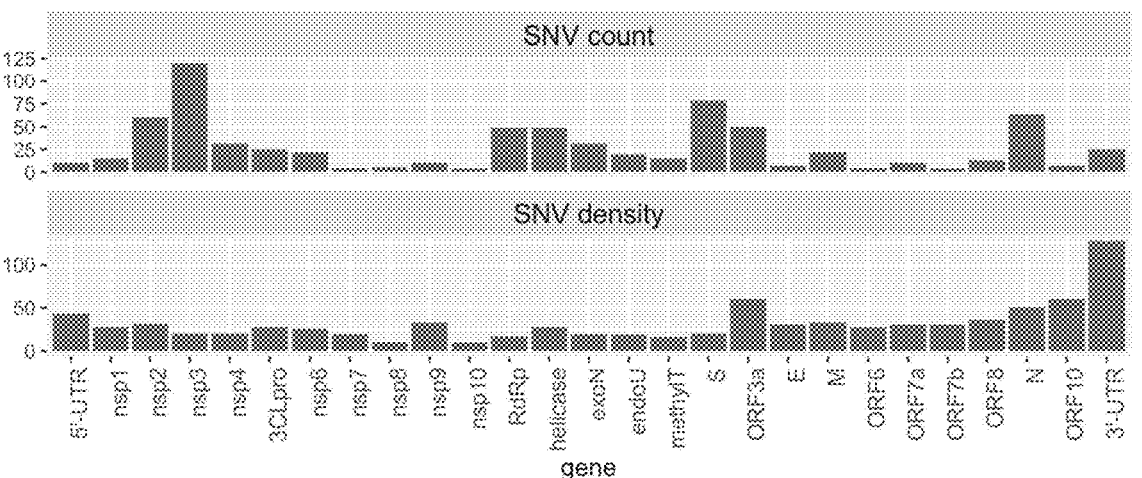

The observed SARS-CoV-2 variants were presumably the result of the evolution of the virus and potential selection pressures on those variants during the pandemic given their likely functional impact on some aspect of the behavior of the virus. Imposing a variant frequency threshold of 0.05% or higher (or, equivalently, occurring in 10 or more genomes) identified 769 SNVs. By considering the number of variant positions per kilobase across gene features, it was found that the 3'-UTR, ORF3a, and the 5'-UTR harbored the highest number of variant positions (FIG. 3A). The next group of genes carrying a high SNV density were ORF10, N, and ORF8, which were all immediately upstream of the 3'-UTR. Two aspects of the 769 SARS-CoV-2 variants were analyzed by classifying the SNVs into the types of observed base changes (i.e. A>T, A>G, A>C, etc.), and amino acid consequences (i.e. missense, synonymous, and nonsense) across the SARS-CoV-2 genes and UTRs. By assigning SNVs into different base change categories, a predominance of C>T mutations out of all 12 possible base changes was observed. The C>T mutation bias in SARS-CoV-2 has been previously suggested to be associated with human host RNA-editing activities and the subsequent fixation of the edited nucleotides in the viral RNA genome. A previous study pointed to C>T/G>A and A>G/T>C variants as base modification outcomes of the human APOBEC and ADAR deaminase family activities, respectively. Results from this gene-by-gene analysis confirmed the study's observations that: (1) C>T variants were the most abundant base change across almost all gene features, and that (2) C>T variants were biased towards the positive-sense RNA strand (FIG. 3B). In other words, C>T variants were more abundant than G>A, which would have been the complementary base changes if C>T variants were to occur in the negative-sense RNA strand. Importantly, these results further revealed that the above two properties did not hold for the 3'-UTR. In the 3'-UTR, it was observed that C>T and G>A variants were similarly frequent, and that G>T variants instead were the most dominant base changes followed by the G>A and C>T variants. These results could indicate different selection pressure or regulation of the 3'-UTR from other parts of the genome. In addition, this analysis also detected G>T variants as the second prominent base change type when considering the entire genome. The gene features showing the highest density of G>T mutations were ORF3a, ORF6, N, and 3'-UTR, all of which were located in the last third of the genome. It was determined that the average G>T variant density in the last third of the genome (downstream of ORF1ab) was three times higher than the first two-thirds of the genome (entire length of the ORF1ab) (FIG. 3B; Fisher's Exact Test, p=2.6e-09). In summary, G>T variants are more enriched towards the 3'-end of the genome.

To investigate whether there are any biases in terms of amino acid (AA) substitutions (i.e. missense, synonymous, and nonsense), it was first determined that, if an SNV occurs randomly at any given nucleotide along the genome, the chances that it results in missense, synonymous, and nonsense mutations would be 73, 22, and 5% respectively. It was also determined that such a distribution remained the same across all 26 protein-coding gene features (FIG. 3C). By analyzing the observed proportions of AA substitutions of the 769 SNVs, lower than expected nonsense and missense variants were detected across all genes with the exception of ORF8. This result suggested likely purifying selection across the protein-coding genes but not on ORF8. Furthermore, it was observed that the deviations of the observed proportions from the expected values varied widely across genes (FIG. 3C). In ORF8, for example, the proportion of missense, synonymous, and nonsense variants were 76.9, 15.4, and 7.7%, respectively, which were similar to expectations. In contrast, for the processed peptide nsp9 (putative function in dimerization and RNA-binding), the corresponding proportions were 18.2, 81.8, and 0%, respectively, revealing fewer missense and nonsense variants than expected. These results suggest that there is likely greatly varying selection and evolutionary pressure on individual SARS-CoV-2 genes. In the nonsense AA setting, only a single nonsense variant out of the 769 SNVs analyzed was detected. The variant was located in ORF8 (p.Q18*). Previous studies have identified multiple variant forms of ORF8 in SARS-CoV and SARS-CoV-related human and animal isolates), including a 29 nt ORF8 deletion variant that had arisen during the late-phase human transmission of SARS-CoV. In summary, the characterization of SARS-CoV-2 variants suggests non-random selection pressure and point to undiscovered driving forces of viral genome evolution originated from the hosts or the virus, which may shed light on the identification of mutations with functional or regulatory roles. Amplicon-based sequencing can be used in the identification of one or more markers for the detection of SARS-CoV-2. Some embodiments of the invention include systems and methods of preparing samples for one or more downstream processes that can be used for assessing one or more markers for the detection of SARS-CoV-2.

Figure 4A:
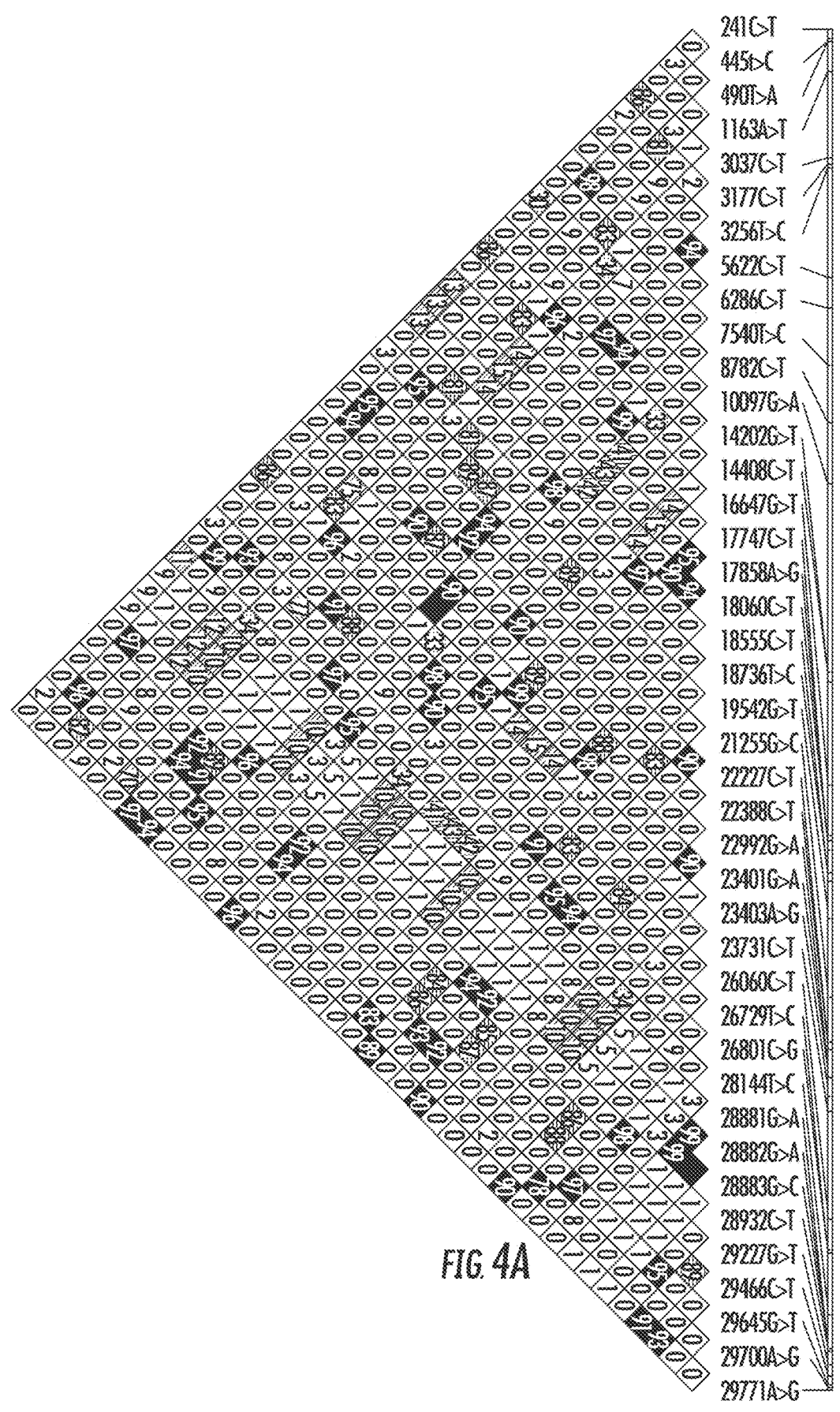
FIGS. 4A and 4B illustrate linkage disequilibrium (LD) plots of co-evolving variant groups.
Figure 4B:
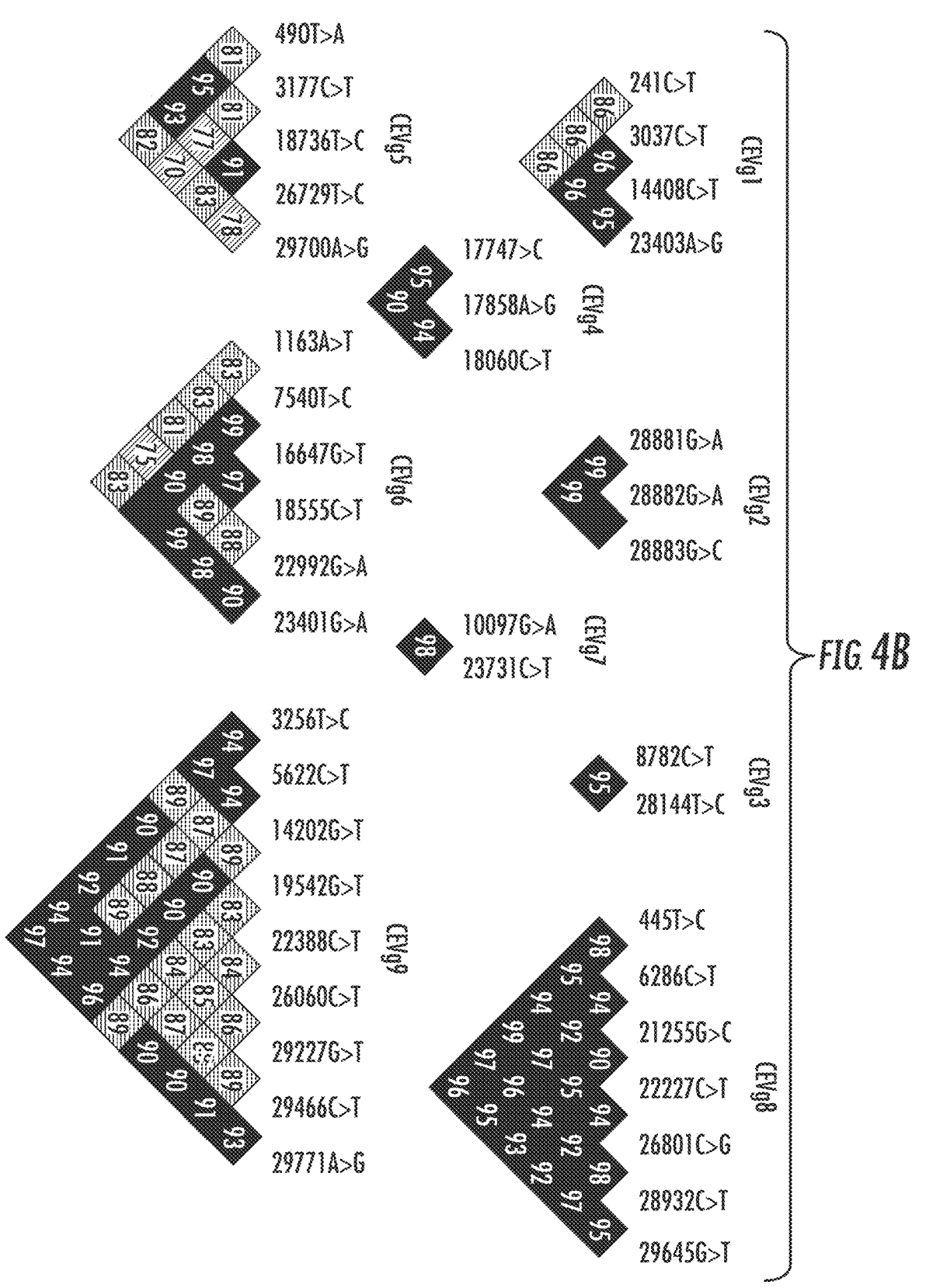

4. Single Nucleotide Variants are Found Across the UTRs and Throughout the Genome Linkage disequilibrium (LD) analysis was performed on SNVs from 18 k GISAID genomes (May 20, 2020 analysis) and 86 k GISAID genomes (Oct. 5, 2020 analysis) using Haploview and identified a total of 34 co-evolving variant groups (referred to as 'CEV' groups) with 0.1% or higher genome frequency (Table 5, FIGS. 4A and 4B).

Figure 5:
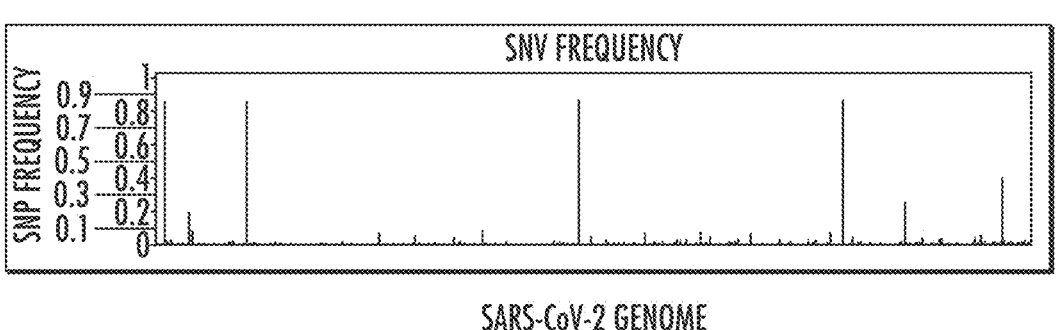
FIG. 5 illustrates SARS-CoV-2 co-evolving SNVs. SNV frequencies are plotted by the positions in the SARS-CoV-2 genome. The relative positions of common SNVs (.0.5%) and 9 representative coevolving variant groups (CEVgs) and amino acid consequences are shown. Variant analysis was based on over 18K genomes (May 29, 2020) and over 86K genomes (Oct. 5, 2020) from GISAID. CEVg1 contains the variants 241C>T (5'-UTR variant), 3037C>T, 14408C>T, and 23404A>G. CEVg2 contains the variants 28881G>A, 28882G>A, and 28883G>C. CEVg3 contains the variants 8782C>T and 28144T>C. CEVg4 contains the variants 17747C>T, 17858A>G, and 18060C>T. CEVg5 contains the variants 490T>A, 3177C>T, 18736T>C, 24034C>T, 26729T>C, and 29700A>G (3'-UTR variant). CEVg6 contains the variants 1163A>T, 7540T>C, 16647G>T, 18555C>T, 22992G>A, and 23401G>A. CEVg7 contains the variants 10097G>A and 23731C>T. CEVg8 contains the variants 445T>C, 6286C>T, 21255G>C, 22227C>T, 26801C>G, 28932C>T, and 29645G>T. CEVg9 contains the variants 3256T>C, 5622C>T, 14202G>T, 19542G>T, 22388C>T, 26060C>T, 29227G>T, 29466C>T, and 29771A>G (3'-UTR variant).

Notably, three CEV groups were identified that involved the UTRs as well as other gene features, which may motivate testable hypotheses about functional dependencies or interactions of the associated features. The first CEV group (CEVg1) was 5'-UTR-associated and detected in 69.5% of SARS-CoV-2 genomes from the May 29, 2020 analysis and in 84.5% of SARS-CoV-2 genomes from the Oct. 5, 2020 analysis. CEVg1 contains four variants that were located in the 5'-UTR (g.241C>T), nsp3 (g.3037C>T, synonymous), the RNA-dependent RNA polymerase (g.14408C>T, p.P323L), and the Spike protein (g.23403A>G, p.D614G) (FIG. 5). In terms of geographic distribution by continent, CEVg1 was predominantly detected in South America (88.2%), Africa (86.8%), Europe (79.6%), North America (66.6%), followed by Oceania (41.6%), and Asia (32.6%). CEVg1 was first detected in an isolate collected on Feb. 20, 2020 in Italy (Italy/CDG1/2020; EPI_ISL_412973) and has since showed a dramatic increase from 12.2% to 93.4% between a 3-month period from February to May 2020. An updated analysis on 25 k GISAID genomes (as of Jun. 13, 2020) identified an earlier isolate that harbored the same set of variants (England/201040021/202; EPI_ISL_464302) collected on Feb. 3, 2020 in the United Kingdom. The increase of CEVg1 was observed both globally and for each region by continent. It has been shown that the Spike protein D614G mutation, one of the variants implicated in CEVg1, is able to infect human cells more efficiently and therefore enhances transmission. The second CEV group (CEVg5) was 3'-UTR-associated and detected in 0.9% of the genomes, and they involved six variants that resided in the leader protein/nsp1 (g.490T>A, p.D75E), nsp3 (g.3177C>T, p.P153L), the exonuclease (g.18736T>C, p.F233L), the Spike protein (g.24034C>T, synonymous), the Membrane protein (g.26729T>C, synonymous), and the 3'-UTR (g.29700A>G). CEVg5 was detected in a low proportion of genomes collected in North America (2.4%), Oceania (2.3%), and Europe (0.1%), and not in other regions. The first such isolate was collected on Mar. 3, 2020 in the US (USA/GA_1320/2020; EPI_ISL_420786). CEVg5 remained as a minor group from March to April, at 1.2, and 0.53%, respectively. The third CEV group (CEVg9) was also 3'-UTR-associated and was detected in 0.8% of the genomes of the Oct. 5, 2020 analysis.

Three additional CEV groups found in more than 5% of the genomes were identified across gene features (FIG. 5). The first of these three, CEVg2, was detected entirely within the N protein in 22.1% of the genomes. CEVg2 consisted of three consecutive variants g.28881G>A, g.28882G>A, g.28883G>C, which together led to two amino acid substitutions, p.R203K and p.G204R, and the change from one to two positively-charged residues. The functional impact of the two amino acid substitutions (p.R203_G204delinsKR) was predicted using PROVEAN, a variant function prediction tool the inventors previously developed. The PROVEAN score of −2.856 suggested a deleterious effect as a result of the two amino acid substitutions. These residues were located within a previously identified region referred to as the nucleocapsid linker region (LKR, residue 182-247 of SARS-CoV). LKR was identified as a flexible region joining the N- and C-terminal modular regions and included one of three intrinsically disordered regions found in the N protein, and may be involved in phosphorylation, oligomerization, and N to M protein interaction. Amongst the 18 k SARS-CoV-2 genomes, the N protein also harbored the highest number of SNV counts per gene feature (i.e. 12 including co-evolving and single SNVs), of which 8 were found to reside within the LKR. CEVg2 was detected in approximately one-third of the genomes collected in Europe (34.7%) and in South America (28.9%) and was also found between 3.7 to 14.0% in other regions. The first occurrence was detected in an isolate collected on Feb. 24, 2020 in Austria (Austria/CeMM0045/2020; EPI_ISL_437932). CEVg2 has since increased in Europe (February to May; 31.9 to 58.9%) and South America (February to April; 0 to 36.5%) but has decreased in Asia and Africa.

The second additional CEV group, CEVg3, included two variants located in nsp4 (g.8782C>T, synonymous) and ORF8 (g.28144T>C, p.L84S), and was found in 11.0% of the genomes (FIGS. 5A and 5B). It has been previously reported by other groups. CEVg3 showed different geographic and temporal profiles than those described above. The first occurrence was detected in an isolate collected in Wuhan on Jan. 5, 2020 (Wuhan/WH04/2020; EPI_ISL_406801). CEVg3 appeared predominantly in North America (23.7%), Oceania (18.7%), Asia (17.0%), and other regions, and showed a declining trend from 32.3, 13.4, to 1.3%, in January, March and May, respectively.

The third additional CEV group, CEVg4, consisted of three variants, two in the helicase (g.17747C>T, p.P504L; g.17858A>G, p.Y541C) and one in the exonuclease (g.18060C>T, synonymous), and was detected in 6.0% genomes (FIGS. 5A and 5B). Both amino acid substitutions in the helicase were predicted to be highly deleterious using PROVEAN (p.P504L, score −8.2; p.Y541C, score −8.9). CEVg4 was first identified from an isolate collected on Feb. 20, 2020 in the United States (Washington), and most positive genomes (92%, 1036 out of 1124) were detected in North America. The per month occurrence of CEVg4 indicated a decrease between February and April from 8.6, 8.0, to 3.3%, respectively.

In addition, the nsp2 processed peptide with unknown function carried the highest number of SNV counts (i.e. 10) after Nucleocapsid. A moderately prevalent nsp2 mutation was detected in 22.9% genomes (g.1059C>T, p.T851), with a predicted deleterious functional outcome (PROVEAN score −4.09) (Table 6). A deletion of three consecutive nucleotides (g.1605_1607delATG) resulting in an amino acid deletion in nsp2 (p.D268del) was predicted to be deleterious (PROVEAN score −6.370). This deletion of 3 nt, although only identified in a small group of 453 genomes (2.4% global collection), appeared to be highly localized in Europe (95%, 428 out of 453 positive genomes), with only few detected in North America (7 genomes) and Oceania (14 genomes). The deletion was first identified in an isolate collected on Feb. 8, 2020 in France (France/RA739/2020; EPI_ISL_410486). A total of 383 genomes were collected from the following regional cluster in proximity: England (124), Netherlands (115), Scotland (102), Northern Ireland (31), and Wales (11). The deletion variant peaked around March in Europe (5.6%) and tapered off in April (2.2%) and May (0.7%). In all, the survey of variant positions across 18,599 SARS-CoV-2 genomes suggested that co-evolving and single variants with likely functional impact on viral fitness or pathogenicity were identified across the UTRs and functional elements throughout the genome.

5. SARS-CoV-2 UTRs and Human miRNAs as Potential Therapeutic Targets

Viral UTRs and human microRNAs have been explored as therapeutic targets in HCV and other viruses because of their essential roles in viral replication and many additional functional phenomena. To gain insight into the possible interplay of the SARS-CoV UTRs with host microRNAs in modulating infection pathogenesis, human miRNAs sharing sequence identity with the UTR sequences of SARS-CoV-2 and SARS-CoV were searched for. miRBase-specific criteria for BLAST analysis was used for this purpose and identified from miRBase (20) a total of 8 and 7 human microRNAs including sense and antisense matching the 3'- and 5'-UTRs, respectively (Table 7). All except one miRNA-

Figure 6A:
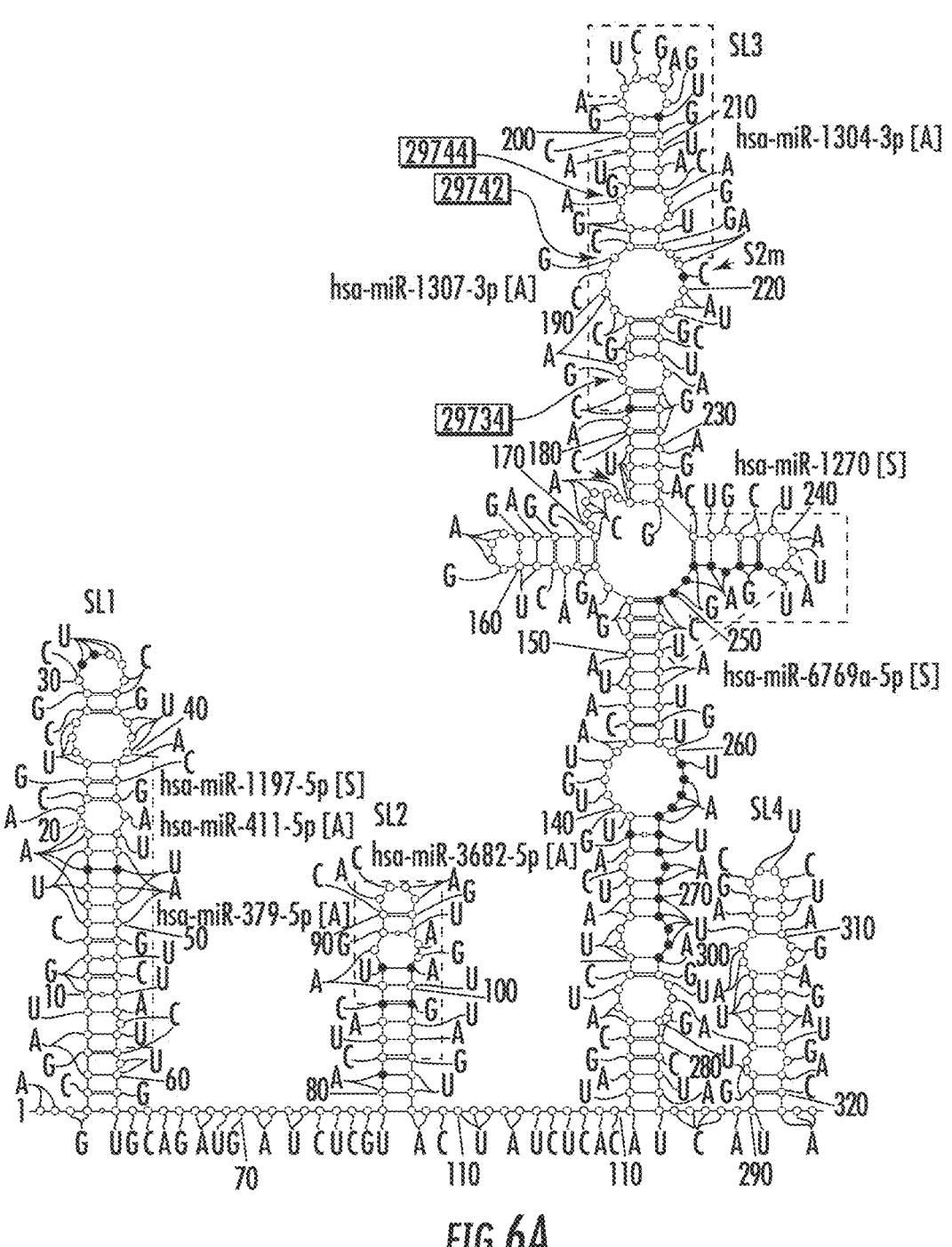

27 matching region (14 out of 15 miRNAs regions) were located on predicted stem-loop structures (FIGS. 6A and 6B). Sequence matches to the human miRNAs hsa-miR-1307-3p and hsa-miR-1304-3p were located within the broader conserved RNA motif S2m. For miR-1307-3p, the predicted minimum energy values for RNA-RNA interac-

28 ing miR-1307-3p for the 3'-UTR. That study provided additional support for a predicted target of human miR-1307-3p in the 3'-UTR of the SARS-CoV-2 genome. Importantly, a previous study of IAV HINI provided supporting functional evidence of hsa-miR-1307-3p in mediating antiviral responses and inhibiting viral replication.

TABLE 7

A list of human miRNAs sharing sequence identities with the UTRs of SARS-CoV and SARS-CoV-2.

| query | subject | % identity | alignment length | mismatches | gap opens | q. start | q. end | s. start | s. end | evalue | bit score | raw score | orientation |
|---|---|---|---|---|---|---|---|---|---|---|---|---|---|
| AY274119.3-5UTR | hsa-miR-5004-3p | 93.33 | 15 | 1 | 0 | 19 | 33 | 16 | 2 | 5.7 | 20.7 | 66 | (−) |
| | hsa-miR-212-5p | 76.19 | 21 | 5 | 0 | 176 | 196 | 2 | 22 | 18 | 19.1 | 60 | (+) |
| | hsa-miR-6837-3p | 87.50 | 16 | 2 | 0 | 92 | 107 | 7 | 22 | 12 | 19.6 | 62 | (+) |
| | hsa-miR-668-3p | 100.00 | 12 | 0 | 0 | 93 | 104 | 1 | 12 | 18 | 19.1 | 60 | (+) |
| | hsa-miR-4798-3p | 92.86 | 14 | 1 | 0 | 118 | 131 | 2 | 15 | 15 | 19.4 | 61 | (+) |
| | hsa-miR-187-3p | 100.00 | 12 | 0 | 0 | 208 | 219 | 10 | 21 | 18 | 19.1 | 60 | (+) |
| | hsa-miR-15b-5p | 83.33 | 18 | 3 | 0 | 223 | 240 | 2 | 19 | 10 | 19.9 | 63 | (+) |
| AY274119.3-3UTR | hsa-miR-1197 | 83.33 | 18 | 3 | 0 | 33 | 50 | 1 | 18 | 13 | 19.9 | 63 | (+) |
| | hsa-miR-379-5p | 88.24 | 17 | 2 | 0 | 33 | 49 | 19 | 3 | 6.1 | 21 | 67 | (−) |
| | hsa-miR-1307-3p | 83.33 | 18 | 3 | 0 | 174 | 191 | 18 | 1 | 13 | 19.9 | 63 | (−) |
| | hsa-miR-1304-3p | 88.24 | 17 | 2 | 0 | 194 | 210 | 19 | 3 | 6.1 | 21 | 67 | (−) |
| | hsa-miR-1270 | 83.33 | 18 | 3 | 0 | 227 | 244 | 1 | 18 | 13 | 19.9 | 63 | (+) |
| | hsa-miR-6769a-5p | 92.86 | 14 | 1 | 0 | 234 | 247 | 8 | 21 | 19 | 19.4 | 61 | (+) |
| NC_045512.2-3UTR | hsa-miR-411-5p | 83.33 | 18 | 3 | 0 | 33 | 50 | 19 | 2 | 14 | 19.9 | 63 | (−) |
| | hsa-miR-3682-5p | 84.21 | 19 | 3 | 0 | 79 | 97 | 19 | 1 | 5.2 | 21.3 | 68 | (−) |
| | hsa-miR-1307-3p | 88.89 | 18 | 2 | 0 | 174 | 191 | 18 | 1 | 2.4 | 22.4 | 72 | (−) |
| | hsa-miR-1270 | 83.33 | 18 | 3 | 0 | 227 | 24 | 1 | 18 | 14 | 19.9 | 63 | (+) |

(+) refers to sense strand;

(−) refers to antisense strand.

tions obtained from RNA22, RNAhybrid, and IntaRNA were 231.1, 237.6, and 220.7 kcal/mol, respectively, all below the commonly considered acceptance threshold of 220 kcal/mol. psRNATarget returned an expectation value (i.e., a penalty for mismatches) of 4, which was below the default and recommended value of 5. TargetScan returned no predictions for miR-1307-3p when considered against the 3'-UTR of SARS-CoV-2, as there is one base mismatch in the middle of the seed region. However, a potential interaction between miR-1307-3p and the 3'-UTR was confirmed by evaluating the target prediction for a 3'-UTR variant (29744G.C). When this base change of interest was introduced at the mismatched position in the wildtype version of the 3'-UTR, a predicted miRNA target of type 7mer-m8 was reported by TargetScan. Furthermore, two recent publications reported results of in silico whole-genome scanning of SARS-CoV-2 to identify candidate human miRNA targets. An earlier publication applied a combination of three miRNA target prediction tools (IntaRNA, miRanda, psR-NATarget) and identified a set of putative miRNAs, includ- The expression of the 15 identified miRNAs was examined using the human miRNA tissue atlas IMOTA, which provided categorized miRNA expression levels (i.e. high, medium, low, or not expressed) for 23 human tissues (Table 8). Among the 8 miRNAs with expression data available, three miRNAs (hsa-miR-1307-3p, hsa-miR-1304-3p, and hsa-miR-15b-5p) were. reported to be expressed mostly at medium level in all 23 tissues including lung, heart, liver, kidney, and small intestine, some of which were reported to be severely affected during the SARS-CoV-2 infection. The expression of miR-1307-3p upon SARS-CoV-2 infection was obtained using the human lung cell line Calu-3 (GEO accession no. GSE148729). From the raw read count data, we determined the trimmed mean of M (TMM) value-normalized expression levels (45) of miR-1307-3p for mock infection and postinfection to be 362.2 and 485.3 cpm, respectively. The expression level of miR-1307-3p increased slightly by 1.3-fold across 4 to 24 h postinfection compared to that after mock infection. Furthermore, the miRBase database was searched to determine whether the 15 identified human miRNAs were conserved in other organisms. While 6miRNAs were not detected in other organisms, 9 miRNAs were found in a number of other mammalian species ranging from 3 to 25 (Table 9). The hsa-miR-1307-3p miRNAs, for example, have been found in 12 other mammalian species in various taxonomic orders such as Primates (e.g. orangutan, chimpanzee, baboon, aye-aye), Artiodactyla (e.g. pig, goat, cow), and others (e.g. bat, dog, rabbit, horse, armadillo). SARS-CoV-2 viral sequences have been detected in dogs from households with confirmed human cases but the dogs remained asymptomatic.

TABLE 9

Number of miRNAs detected in other organisms in miRBase database grouped by taxonomic class. Search conditions required 18 or more matching nucleotides and allowing gaps, and the number includes the human miRNA itself.

| Region | human miRNA | Actinopteri | Amphibia | Aves | Mammalia | No class name in Chordata | Grand Total |
|--------|-------------|-------------|----------|------|----------|---------------------------|-------------|
| 5UTR | hsa-miR-15b-5p | 18 | 7 | 9 | 57 | 12 | 103 |
| 5UTR | hsa-miR-187-3p | 12 | 1 | 3 | 22 | 3 | 41 |
| 5UTR | hsa-miR-212-5p | 11 | 1 | 2 | 14 | 5 | 33 |
| 5UTR | hsa-miR-668-3p | | | | 7 | | 7 |
| 5UTR | hsa-miR-4798-3p | | | | 3 | | 3 |
| 5UTR | hsa-miR-6837-3p | | | | 1 | | 1 |
| 5UTR | hsa-miR-5004-3p | | | | 1 | | 1 |
| 3UTR | hsa-miR-411-5p | | | | 22 | | 22 |
| 3UTR | hsa-miR-379-5p | | | | 20 | | 20 |
| 3UTR | hsa-miR-1307-3p | | | | 13 | | 13 |
| 3UTR | hsa-miR-1197 | | | | 12 | | 12 |
| 3UTR | hsa-miR-1304-3p | | | | 4 | | 4 |
| 3UTR | hsa-miR-1270 | | | | 2 | | 2 |
| 3UTR | hsa-miR-6769a-5p | | | | 1 | | 1 |
| 3UTR | hsa-miR-3682-5p | | | | 1 | | 1 | hsa-mir-1307 and hsa-mir-1304 are the human microRNA targets identified herein as potential therapeutic targets. The precursor sequence for hsa-mir-1307 is (SEQ ID NO: 11)
CAUCAAGACCCAGCUGAGUCACUGUCACUGCCUACCAAUCUCGACCGG

ACCUCGACCGGCUCGUCUGUGUUGCCAAUCGACUCGGCGUGGCGUCGG

UCGUGGUAGAUAGGCGGUCAUGCAUACGAAUUUUCAGCUCUUGUUCUG

GUGAC, with its corresponding mature sequence bolded and underlined (SEQ ID NO:12). The precursor sequence for hsa-mir-1304 is (SEQ ID NO: 13)
AAACACUUGAGCCCAGCGGUUUGAGGCUACAGUGAGAUGUGAUCCUGC

CACAUCUCACUGUAGCCUCGAACCCCUGGGCUCAAGUGAUUCA, with its corresponding mature sequence bolded and underlined (SEQ ID NO: 14). The identified candidate host microRNA, any of SEQ ID NOS: 11-14, could be targeted by antisense oligonucleotides to inhibit an infection caused by a coronavirus, including SARS-CoV-2. Thus, an antisense oligonucleotide which targets at least one of microRNA-1307 (hsa-mir-1307) or hsa-mir-1304 is a potential treatment construct for a coronavirus infection in a subject.

The search for therapeutic constructs further includes microproteins having characteristics that could bind to a human channel to form a non-functional complex. The SARS-CoV-2 virus and the human proteomes are screened for similarities based on amino acid sequence and secondary structure. A pharmaceutical composition, such as a small molecule, targeting one of the stem-loop structures of Region 1 or Region 2, identified throughout this disclosure as s2m, may be used to inhibit an infection caused by a coronavirus, including SARS-CoV-2. Thus, other pharmaceutical compositions which target at least one of the s2m structures in Region 1 or Region 2 have the potential to disrupt the viral activity of the coronavirus, including SARS-CoV-2.

6. Targeted Amplicon Sequencing

In addition to PCR, amplicon-based sequencing can be used in the identification of one or more markers for the detection of SARS-CoV-2, human SARS-CoV, and other non-human coronaviruses. For a targeted amplicon sequencing method, amplicon library preparation may be performed using the universal tail indexing strategy, i.e., using primers having universal tails. A universal indexing sequencing strategy can be used to amplify multiple genomic regions (e.g., markers, as described) from a sample simultaneously in a single reaction for the sequencing of one or more amplicons. Some embodiments of the invention comprise multiple steps and/or processes that are carried out to execute the universal tail indexing strategy to prepare amplicons for sequencing.

The amplicon sequencing method may include creating a series of oligonucleotides designed to provide multiplexed amplification of one or more markers to produce the desired amplicons. After production of the amplicons (e.g., via PCR amplification), which may include the universal tail sequences (using primers having universal tails), the resulting amplicons can be further processed to provide sequencing-ready amplicons. A universal indexing sequencing strategy can be used to amplify multiple genomic regions (e.g., markers, as described below) from a DNA sample simultaneously in a single reaction for the sequencing of one or more amplicons. The method may further include performing downstream sequencing on the sequencing-ready amplicons. Some embodiments of the invention comprise multiple steps and/or processes that are carried out to execute the universal tail indexing strategy to prepare amplicons for sequencing.

In certain embodiments, the amplicon library preparation comprises two PCR steps, a gene-specific multiplex PCR and an index extension PCR.

First PCR: In gene-specific multiplex PCR reactions, the target amplicons are synthesized with a universal tail sequence added to the amplicons. Each primer includes a gene-specific sequence and a universal tail sequence. In certain implementations, the forward primers have a first universal tail sequence, and the reverse primers have a second universal tail sequence, with the second universal tail sequence being different than the first universal tail sequence. The amplification of the target results in the production of amplicons that comprise the first and second universal tail sequences integrated therein. After production of the amplicons during the multiplex PCR assay, the resulting amplicons can be further processed an indexing extension step to provide sequencing-ready amplicons.

Second PCR: The indexing extension PCR adds a specific index sequence to the amplicons using the universal tail sequences on either end of the amplicon. Stated differently, the amplicons are extended using platform-specific primers that recognize at least one of the universal tail sequences for adding the indexes to each amplicon. The index is unique for each sample, such that the indexing primer includes a sample-specific index sequence and a common universal tail complement sequence. Thus, the number of different indexing primers used in the second PCR depends on the number of unique samples being processed in the same PCR. Each indexing primer comprises a complementary sequence that recognizes at least one of the first universal tail sequence and the second universal tail sequence that has been previously integrated within the amplicons. At the end of the index extension PCR there is a sequencer-ready amplicon library. By adding sample specific index sequences to the amplicons, pools of several samples are made ready for sequencing. The samples can be pooled for sequencing using a desired platform during a single sequencing run and distinguished based on the index sequence during analysis of the data. The inclusion of the universal tail sequences (on the index and common primers may coincide with the use of genomic and index read primers in the mixture of sequencing primer reagents. After sequencing, the resulting data can be de-multiplexed and the sequence files can be aligned to a reference sequence (e.g., a wild type sequence and/or other alleles for each of the respective markers) for subsequent sequence analyses. As a result, the aligned sequences can be analyzed for the presence or absence of markers, variant signatures associated with the markers, differential marker presence in the sample, which includes the capability of analyzing gene expression, and an estimate of allele frequencies of various alleles of the markers in the pooled samples.

For example, the second PCR, using the universal tail-specific primers, adds Illumina's sample-specific index and sequencing adapters. Samples may then be pooled in equimolar concentration for sequencing. The amplicons may be sequenced by next-generation sequencing using a desired platform, such as the Illumina® MiSeq platform. Methods of sequencing include but need not be limited to any form of DNA sequencing including Sanger, next-generation sequencing, pyrosequencing, SOLID sequencing, massively parallel sequencing, pooled, and barcoded DNA sequencing or any other sequencing method now known or yet to be disclosed. The number or quantity of sequencing reads for a particular gene or marker can be counted for each sample. In some aspects, the amplicons resulting from the multiplex PCR reaction can be sequenced, and the resulting sequences can be aligned to a reference sequence. As a result, differential numbers of sequence reads generated by the sequencing process (i.e., when aligned to the amplicon reference sequences), can provide data regarding the different copy numbers in the original RNA sample. The sequencing data or sequencing reads can be analyzed for identification and detection of coronavirus.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

---

What is claimed is:

1. A method of detecting severe acute respiratory syndrome coronavirus 2 (SARS-COV-2) in a sample, comprising:
   extracting nucleic acids from the sample;
   amplifying a 3' untranslated region (UTR) of a betacoronavirus lineage B genome to produce an amplification product; and
   detecting in the amplification product the presence or absence of one or more single nucleotide polymorphisms (SNPs) specific to SARS-COV-2, wherein the one or more SNPs correspond to a nucleotide position of the betacoronavirus lineage B genome selected from the group consisting of position 29567, position 29581, position 29582, position 29597, position 29631, position 29635, position 29637, position 29649, position 29651, position 29688, position 29732, position 29735, position 29758, and position 29769,
   wherein the nucleotide positions follow the SARS-COV-2 Wuhan-Hu-1 reference isolate (NCBI Reference Sequence: NC 045512.2).

2. The method of claim 1, wherein the one or more SNPs are selected from the group consisting of:
   an A at position 29567,
   a T at position 29581,
   a T at position 29582,
   a T at position 29597,
   an A at position 29631,
   a C at position 29635,
   a T at position 29637,
   an A at position 29649,
   a G at position 29651,
   a G at position 29688,
   a C at position 29732,
   an A at position 29735,
   a T at position 29758, and
   a C at position 29769.

3. The method of claim 1, further comprising administering a therapeutically effective amount of an anti-viral composition to the subject based on the presence of SARS-COV-2 in the sample.

4. The method of claim 3, wherein the method comprises:

receiving the sample from a subject;

extracting nucleic acids from the sample;

adding a plurality of primers to a mixture containing the sample, subjecting the mixture to conditions sufficient to amplify a 3' untranslated region (UTR) of the beta-coronavirus lineage B genome to produce an amplification product, wherein the plurality of primers comprises at least one primer that hybridizes under hybridizing conditions to an amplified 3'UTR comprising a nucleotide signature, referring to SEQ ID NO: 1, selected from the group consisting of:

an A at position 29567, a T at position 29581, a T at position 29582, a T at position 29597, an A at position 29631, a C at position 29635, a T at position 29637, an A at position 29649, a G at position 29651, a G at position 29688, a C at position 29732, an A at position 29735, a T at position 29758, and a C at position 29769;

detecting the presence or absence of the amplification product, wherein the presence of the amplification product is indicative of the presence of SARS-COV-2 in the sample and wherein the absence of the amplification product is indicative of the absence of SARS-COV-2 in the sample; and administering a therapeutically effective amount of an anti-viral composition to the subject based on the presence of the SARS-COV-2 in the sample.

5. The method of claim 3, wherein the anti-viral composition comprises an antisense oligonucleotide or a small interfering RNA (siRNA).

6. The method of claim 5, wherein the siRNA targets SEQ ID NO: 1.

7. The method of claim 3, wherein the anti-viral composition comprises an inhibitor of hsa-mir-1307 or an inhibitor of hsa-mir-1304.

8. The method of claim 7, wherein the inhibitor of hsa-mir-1307 comprises an antisense oligonucleotide which targets hsa-mir-1307 and the inhibitor of hsa-mir-1304 comprises an antisense oligonucleotide which targets hsa-mir-1304.

\* \* \* \* \*